United States Patent
Gottschall et al.

(10) Patent No.: US 11,059,856 B2
(45) Date of Patent: Jul. 13, 2021

(54) USE OF A POLYMERIC MESH FOR THE PURIFICATION OF MACROMOLECULES

(71) Applicant: Klawego GmbH & Co. KG, Heddesheim (DE)

(72) Inventors: Klaus Gottschall, Heddesheim (DE); Lothar Britsch, Reute (DE); Evelyn Gottschall, Heddesheim (DE)

(73) Assignee: Klawego GmbH & Co. KG, Heddesheim (DE)

( * ) Notice: Subject to any disclaimer, the term of this patent is extended or adjusted under 35 U.S.C. 154(b) by 147 days.

(21) Appl. No.: 16/333,637

(22) PCT Filed: Sep. 15, 2017

(86) PCT No.: PCT/EP2017/073332
§ 371 (c)(1),
(2) Date: Mar. 15, 2019

(87) PCT Pub. No.: WO2018/050849
PCT Pub. Date: Mar. 22, 2018

(65) Prior Publication Data
US 2019/0256554 A1      Aug. 22, 2019

(30) Foreign Application Priority Data
Sep. 15, 2016   (EP) .................................. 16189065

(51) Int. Cl.
*B01D 15/34* (2006.01)
*B01J 20/26* (2006.01)
(Continued)

(52) U.S. Cl.
CPC .............. *C07K 1/165* (2013.01); *B01D 15/34* (2013.01); *B01J 20/267* (2013.01); *B01J 20/285* (2013.01);
(Continued)

(58) Field of Classification Search
CPC ... B01D 15/34; B01J 20/267; B01J 20/28042; B01J 20/28083; B01J 20/28085;
(Continued)

(56) References Cited

U.S. PATENT DOCUMENTS

2009/0050566 A1*   2/2009   Kozlov .................... B01J 47/12
                                                            210/656

FOREIGN PATENT DOCUMENTS

| EP | 2027921 A2 | 2/2009 |
| WO | 2013007793 A1 | 1/2013 |
| WO | 2013007799 A1 | 1/2013 |

OTHER PUBLICATIONS

International Searching Authority, Search Report issued in International Application No. PCT/EP2017/073332 dated Feb. 16, 2018 (2 pages).

* cited by examiner

*Primary Examiner* — Pranav N Patel
(74) *Attorney, Agent, or Firm* — Wood Herron & Evans LLP

(57) ABSTRACT

Method for recovering a target protein from a feedstock comprising said target protein and at least one impurity compound selected from host cell proteins (HCP), DNA, RNA or other nucleic acid, the target protein being characterized by a hydrodynamic radius $R_{h1}$ and the impurity compound being characterized by a hydrodynamic radius $R_{h2}$, wherein $R_{h1} > R_{h2}$, comprising the following steps (i) to (iv) and optionally step (v): (i) providing a polymeric mesh comprising at least one crosslinked polymer containing positively charged amino groups, wherein the polymer has a pore size exclusion limit Rhi which can be set variably; (ii) adapting the variable pore size exclusion limit Rhi of the polymeric mesh such that $R_{h2} < R_{hi}$ and $R_{h1} > R_{hi}$; (iii) contacting the polymeric mesh with the feedstock; (iv) separat-
(Continued)

Fig. Embodiment 1.1 ing the polymeric mesh containing the retained impurity compound from the feedstock containing the excluded target protein.

20 Claims, 16 Drawing Sheets

(51) Int. Cl.
*B01J 20/28* (2006.01)
*B01J 20/285* (2006.01)
*B01J 20/30* (2006.01)
*C07K 16/42* (2006.01)
*C07K 1/34* (2006.01)
*C07K 1/16* (2006.01)
*C07K 1/18* (2006.01)
*C07K 1/22* (2006.01)
*C07K 16/00* (2006.01)

(52) U.S. Cl.
CPC ... *B01J 20/28042* (2013.01); *B01J 20/28088* (2013.01); *B01J 20/28097* (2013.01); *B01J 20/3085* (2013.01); *C07K 1/18* (2013.01); *C07K 1/22* (2013.01); *C07K 1/34* (2013.01); *C07K 16/00* (2013.01); *C07K 16/42* (2013.01); *B01J 20/28083* (2013.01); *B01J 20/28085* (2013.01)

(58) Field of Classification Search
CPC .......... B01J 20/28088; B01J 20/28097; B01J 20/285; B01J 20/3085; C07K 16/00; C07K 16/42; C07K 1/165; C07K 1/18; C07K 1/22; C07K 1/34

See application file for complete search history.

Fig. Embodiment 1.1

Elution volume $V_e$ versus the hydrodynamic radii $R_h$ of the Pullulane

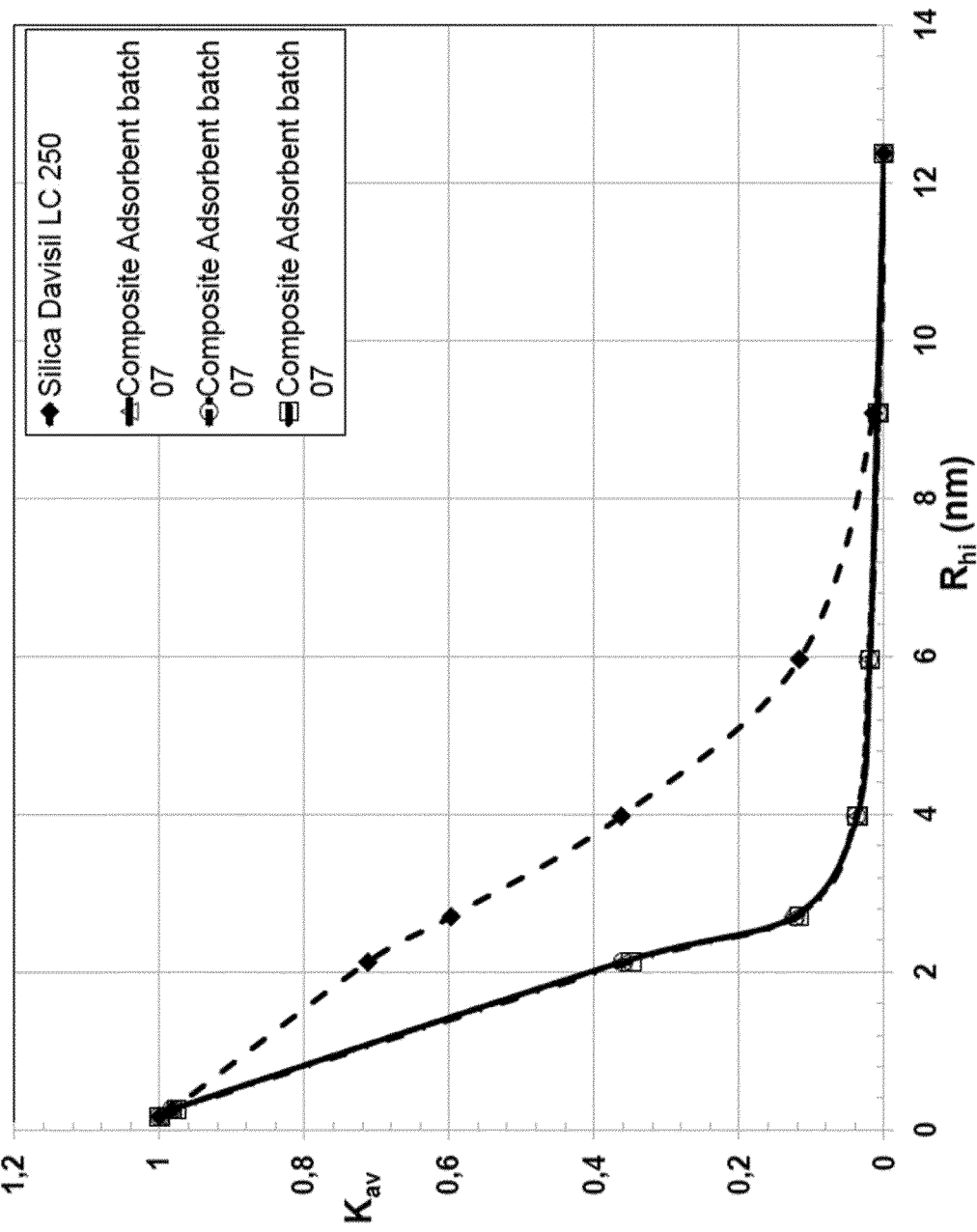

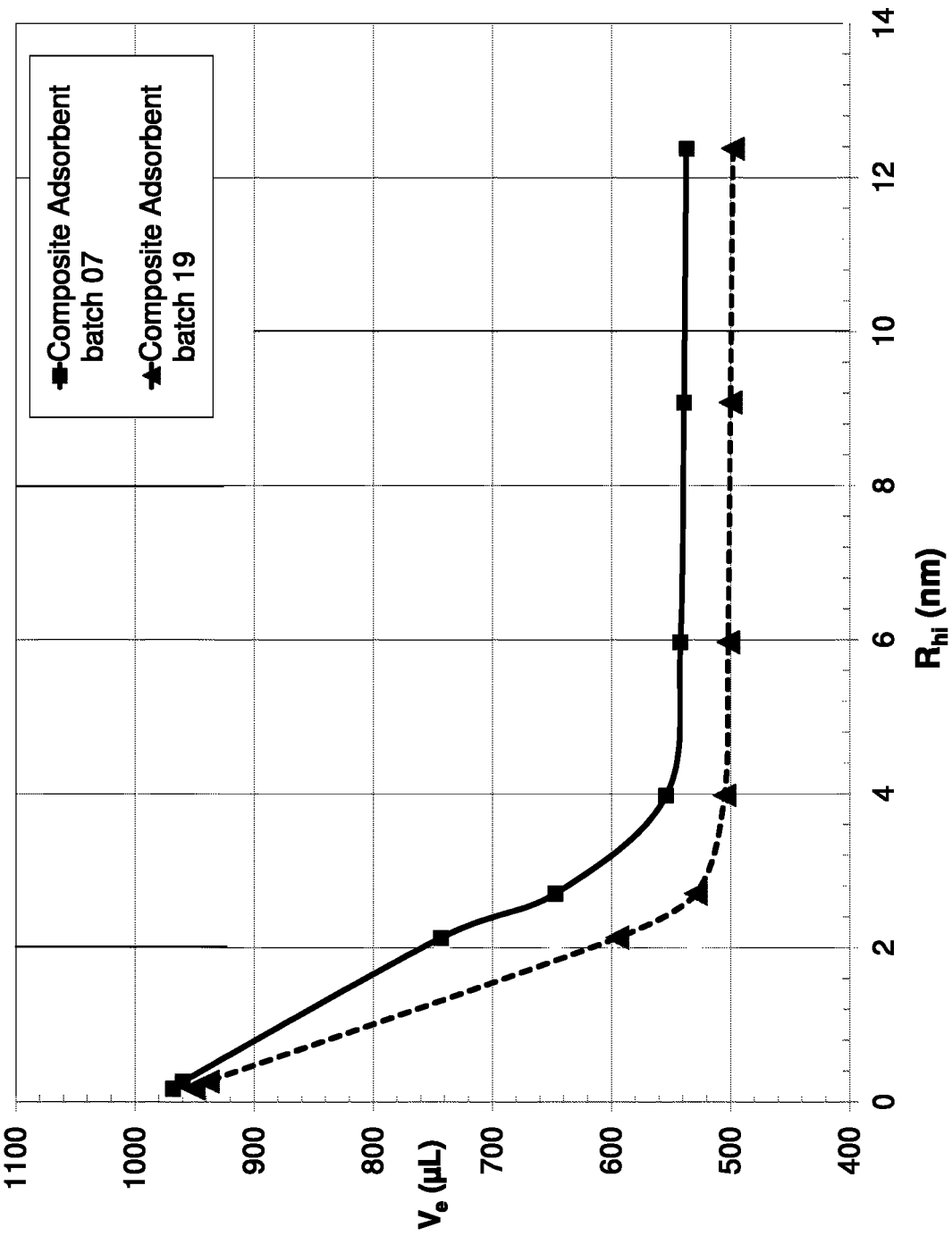

Distribution Coefficient $K_{av}$ versus the hydrodynamic radii $R_h$ of the Pullulanes Fig. Embodiment 1.4

IEF of CCS CHO-K1 – 12.5 fold concentrated

IEF Standards - BioRad in the same run under the same conditions

Exclusion of hIgG from the adsorbent pores according to Example 3, while only a minor portion is bound to the exterior surface of the adsorbent.

Figure 4:
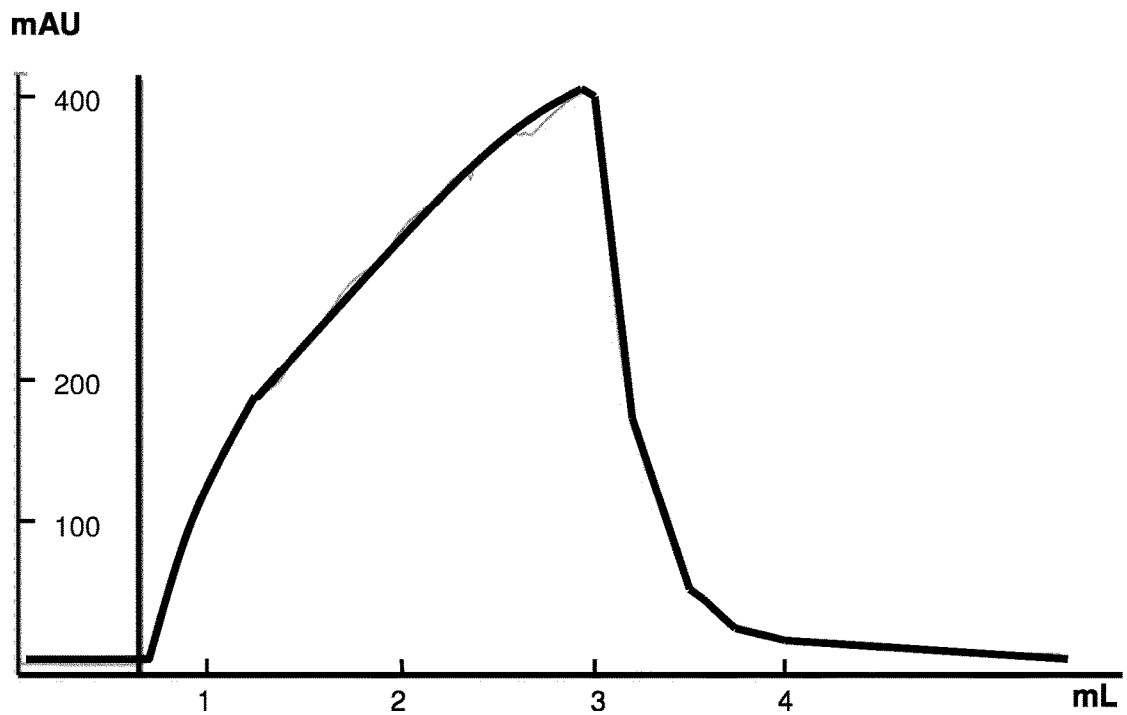
Figure 5:
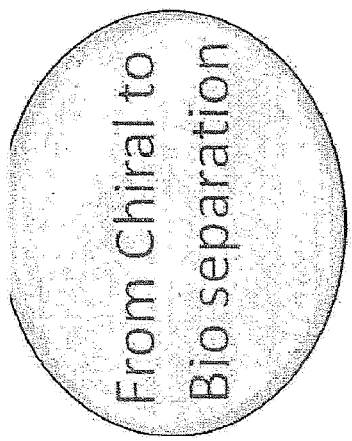
Figure 6:
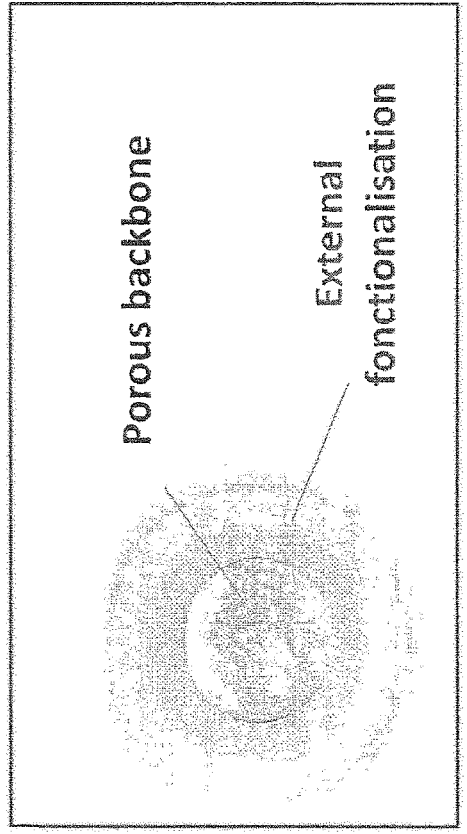
Figure 6:
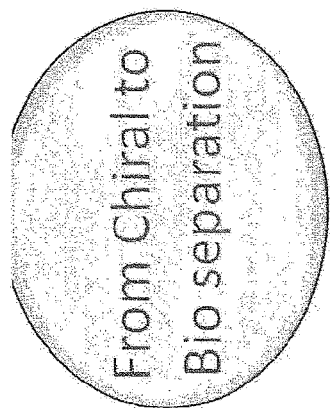
Figure 7:
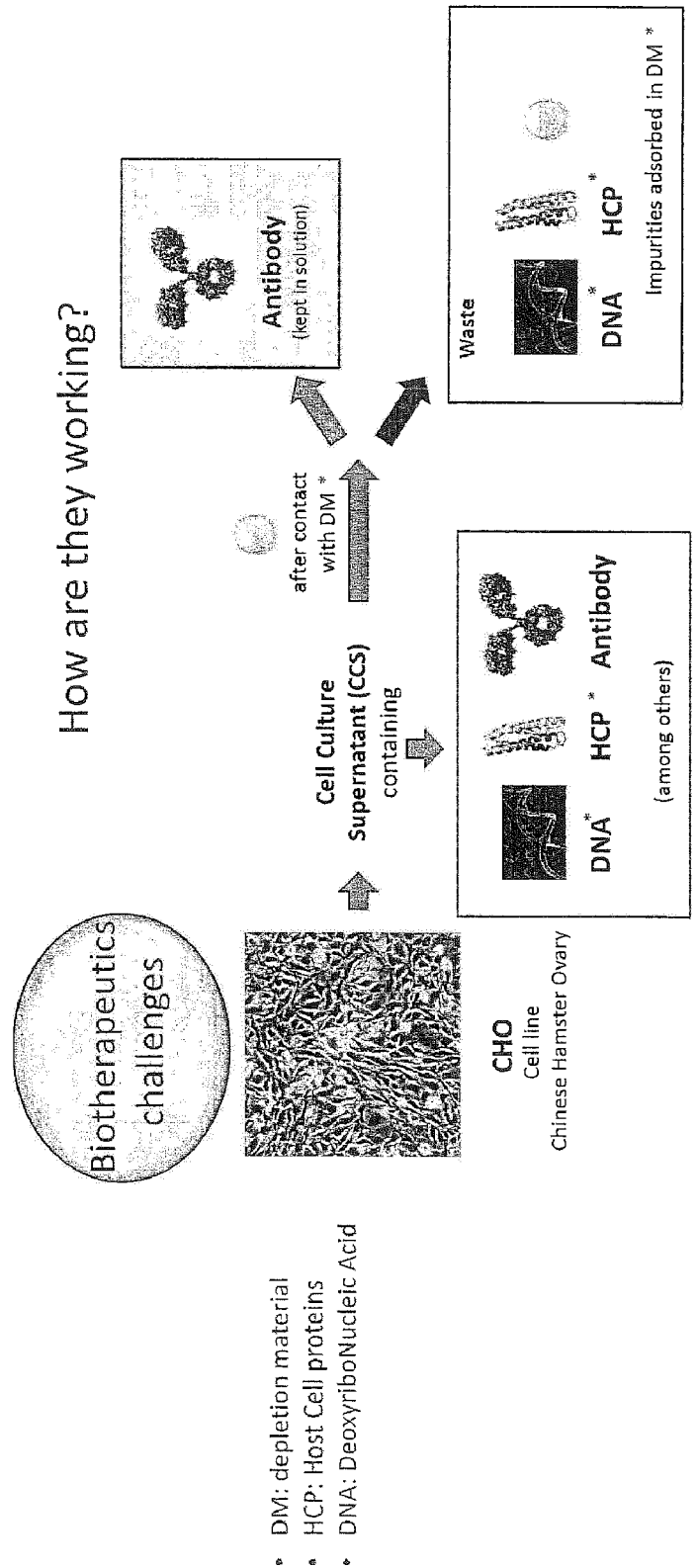
Figure 8:
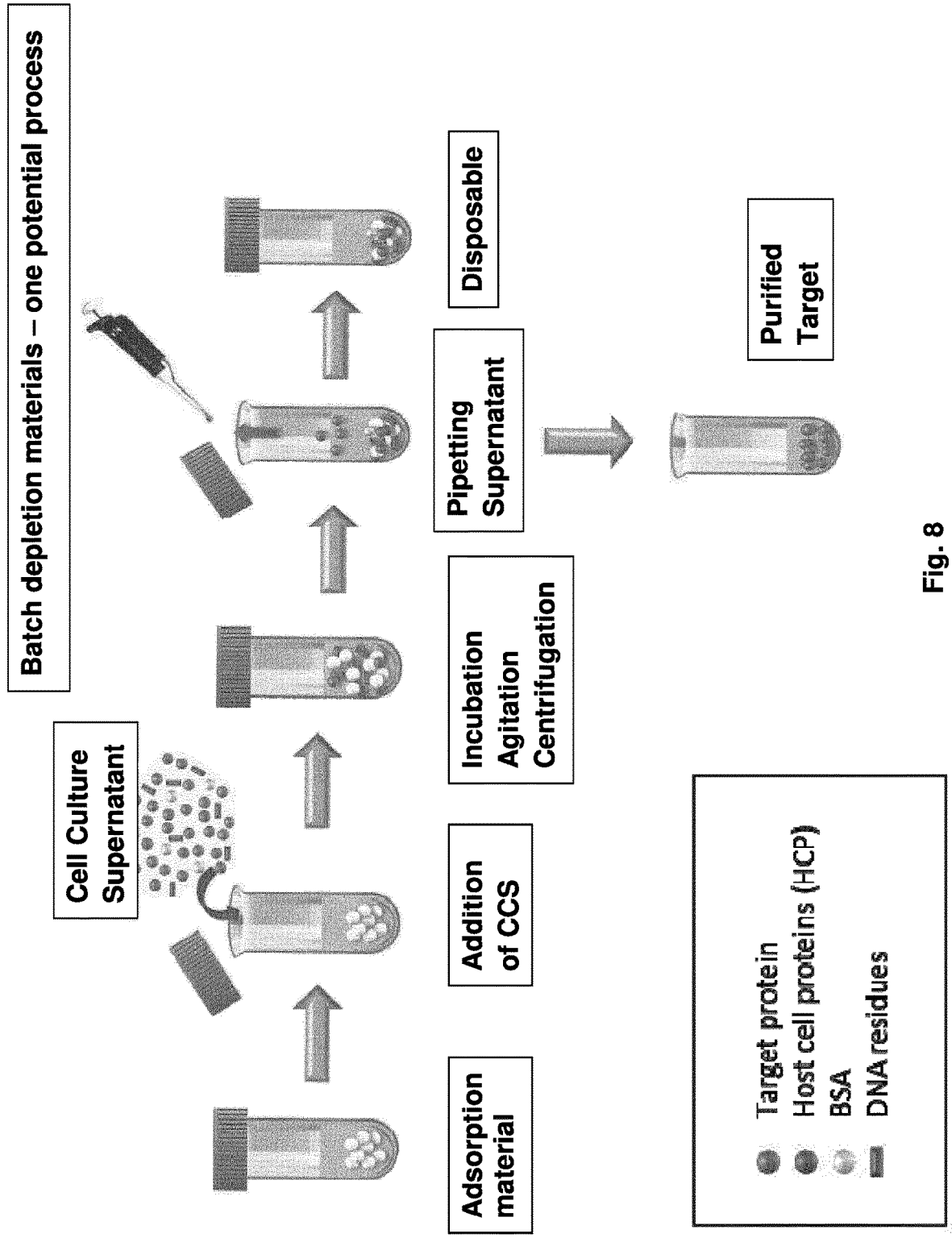
Figure 9:
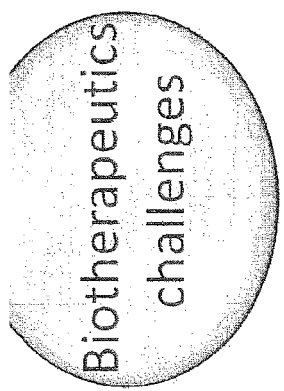
Figure 9:
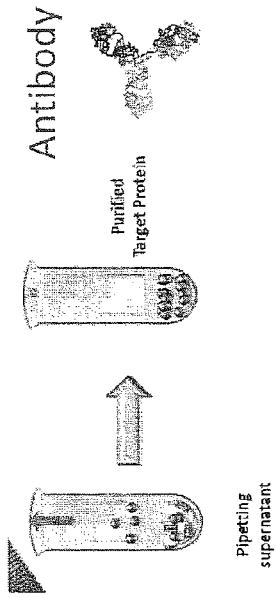
Figure 9:
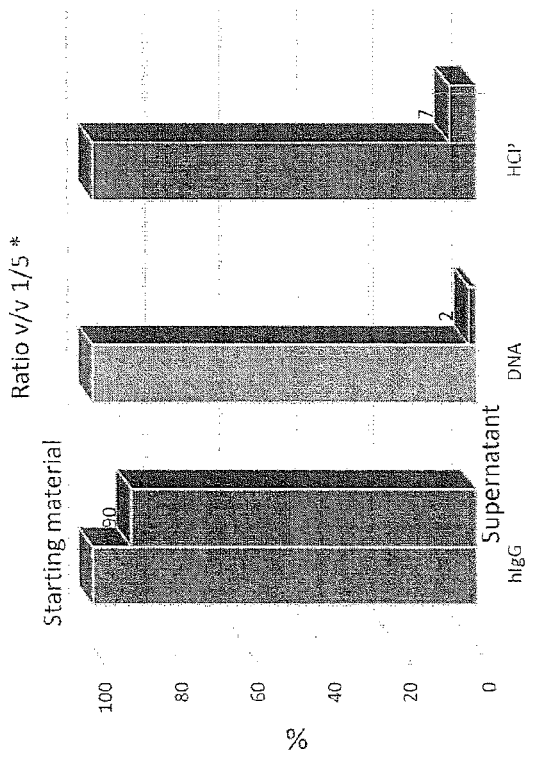
Figure 10:
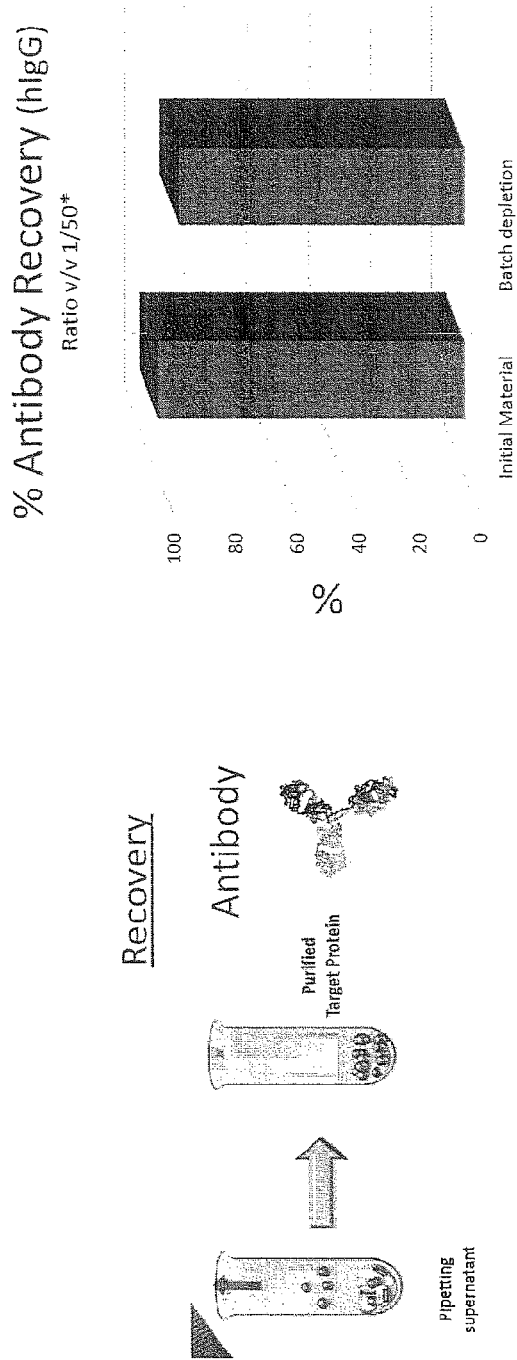
Figure 10:
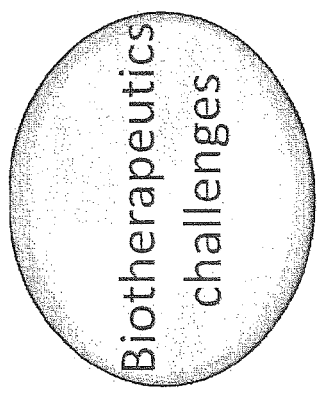
Figure 11:
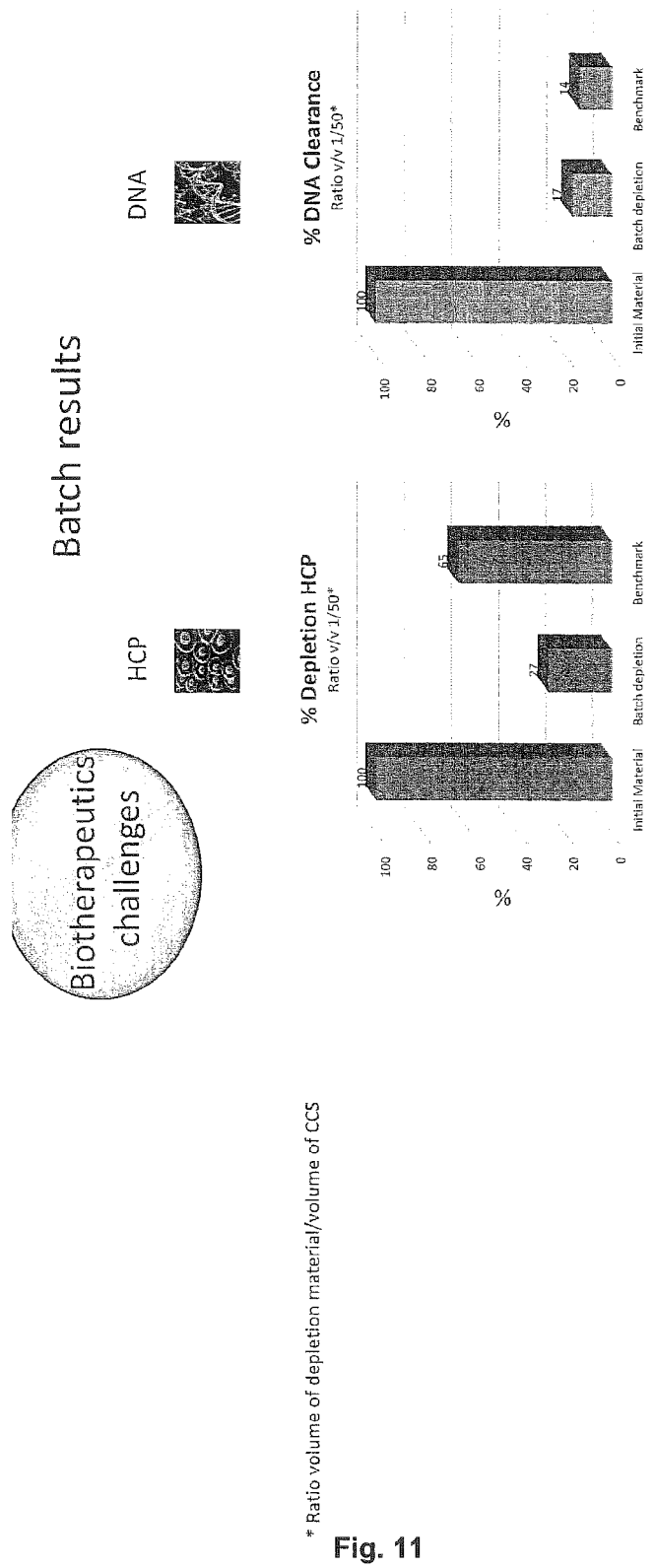
Figure 12:
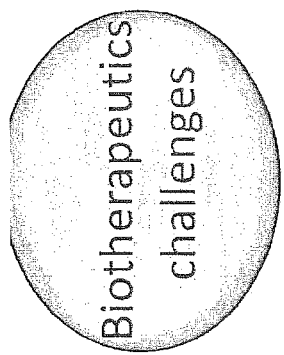
Figure 12:
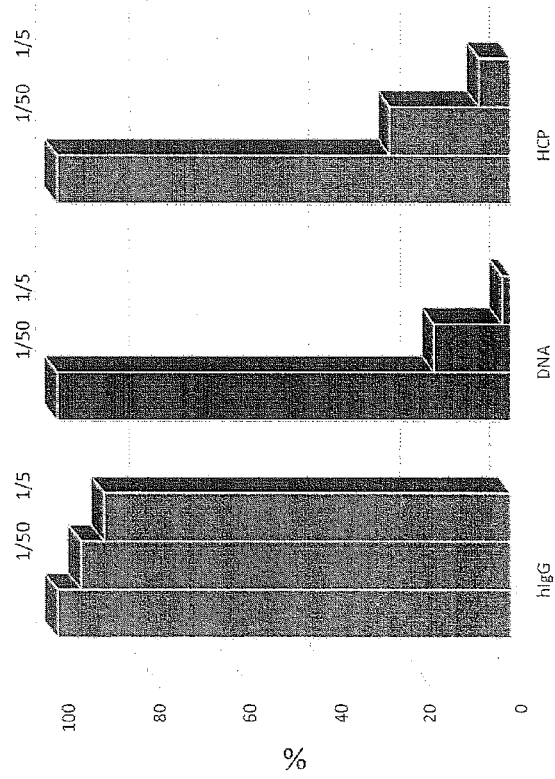

Fig 4.1    Determination of the dynamic hIgG capacity

The hIgG solution was loaded at a flow rate of 0.2 mL/min and washed out at 1 mL/min with the buffer.

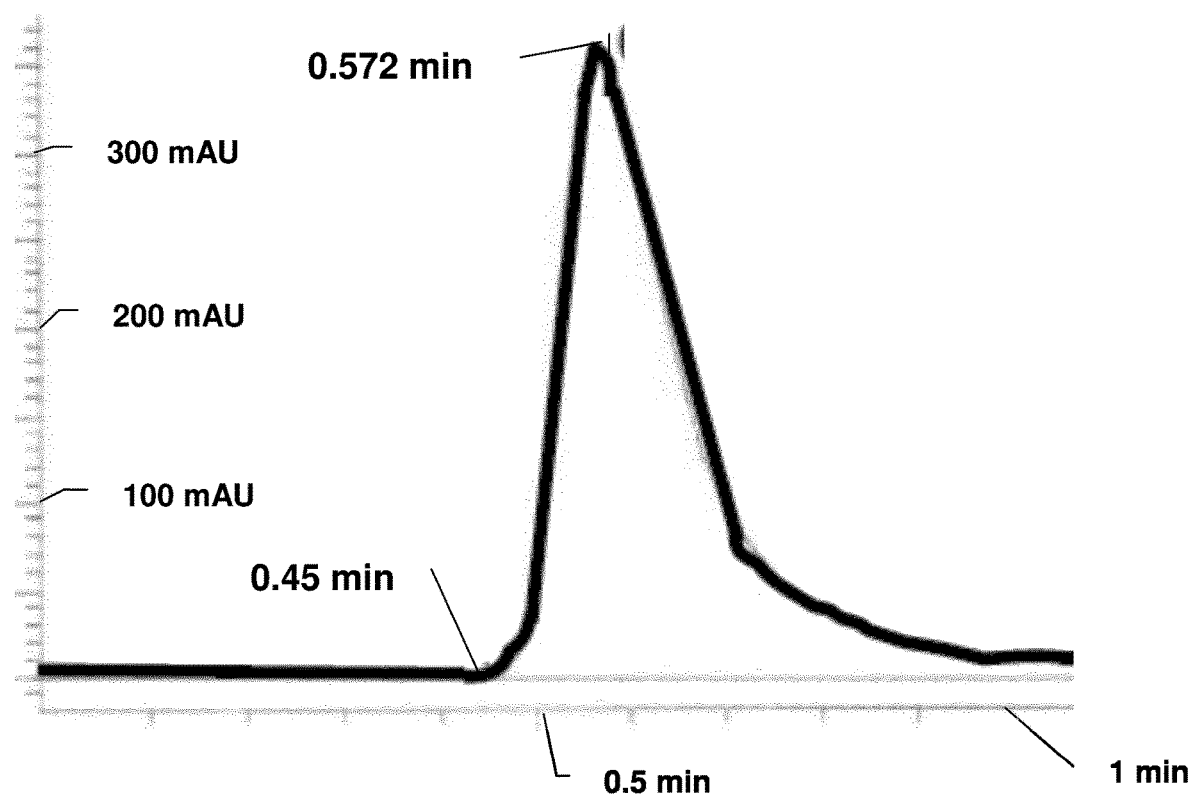
Figure 4.2  No further hIgG binding after saturation

Our Objectives

From Chiral to Bio separation

✓ Design of salt tolerant material able to work at physiological pH

✓ Design of material effective for
    mAb purification,
    mAb fragments,
    any type of proteins,
    viruses, ...

✓ Applications at
    lab scale
    large scale processes

USE OF A POLYMERIC MESH FOR THE PURIFICATION OF MACROMOLECULES

TECHNICAL FIELD

The present invention relates to the use of a polymeric mesh, comprising either polymer gels or composite materials for separating undesired compounds from a solution or suspension containing said undesired compounds and a target compound. The present invention also relates to a particular polymeric mesh suitable for this purpose, and to a process for the preparation of composite materials comprising said polymeric mesh. The present invention also relates to a method for recovering a target protein from a fermentation broth using said polymeric mesh. In particular, the present invention relates to the separation of recombinant proteins, preferably antibodies and antibody fragments, by use of said composite material.

BACKGROUND OF THE INVENTION

Purified soluble macromolecules are very important substances throughout the industries. Mainly the pharmaceutical and medical areas are reporting a growing need for bio-polymeric substances, primarily for therapeutic and diagnostic purposes, but also for technologies like tissue engineering. Among the available chromatographic methods size exclusion chromatography (SEC) is not considered useful for large scale operations, except for polishing purposes, due to the notoriously low productivity, caused by low capacity, low resolution and low speed. In particular, the loading capacity in SEC is generally very limited, because the separation of molecules according to their size takes place within a maximum of one total liquid volume inside a packed column. Thereby the ratio between interstitial volume and pore volume of the specific stationary phase, as well as the pore size distribution, are major characteristics contributing to the limited sample volume in SEC.

Due to the huge number of different impurities in raw solutions of macromolecules, e.g. crude extracts from almost all kinds of biological starting materials, particularly those from living or dead tissues, tissue and cell cultures of various cultivation techniques, the first step in a conventional chromatographic purification process is usually comprising the binding of the target compounds ("capture"), whereas the majority of undesired products is left unbound at all or may be separated from the target by a selective elution step, releasing bound impurities before or after the target substance during this step.

It would be highly advantageous, however, in terms of product recovery and overall process streamlining, to bind the majority of impurities in a first step, whereas the purified target compound remains unbound in the solution. Mainly for the purpose of antibody purification this approach should allow to bind the majority of accompanying proteins which are present in the raw feed solution, exhibiting molecular weights between approximately 10,000 Da. and 100,000 Da. This molecular mass range of proteins corresponds to molecular sizes between approximately 1.5 nm and 5 nm hydrodynamic radius $R_h$.

Corresponding problems were not generally solved in this way by the prior art.

For the purification of antibodies and other proteins a few methods have been reported using composite adsorbents as a separation agent, comprising various support materials and amino polymers. Support materials were either particles, filter media, or membranes. Polyethylene imine, poly(allylamine) and poly(vinylamine) have been the preferred functional amino polymers, attached to the support either covalently or after cross-linking.

For this purpose, basically chromatographic methods have been applied characterized in that a filter material or a packed bed with particles is perfused with various buffers for binding and elution, while certain compounds of the feed are retained.

With respect to the particle based composite materials the patent application family of WO 2013/007793 A1, WO 2013/007799 A1, WO 2013/037991 A1, WO2013/037992 A1, WO 2013/037993 A1, WO 2013/037994 A1, WO 2013/037995 A1 ("WO 994" family) is comprising the coating of spherical silica and polystyrene sulphonate supports with polyvinyl amine of unknown origin. Usually these composites have been further derivatized, dedicated to a selective separation of various drug compounds. The attachment of the poly(vinylamine) coating was generally achieved by a two-step procedure: The support material was soaked with the aqueous polymer solution, including the pores, followed by drying this material. In the second step, the cross-linking was carried out in suspension after dissolving the cross-linker in an appropriate organic solvent, which does not dissolve the precipitated polymer again.

WO 90/14886 discloses a composite separation medium for use in protein separation comprising a matrix carrying a plurality of polyamines which are covalently attached to the matrix.

WO 95/25574 relates to a method for removing contaminants from a biological fluid comprising bringing said biological fluid into contact with a cross-linked hydrophobic polymeric mesh overlaying, but not covalently bound to, a porous mineral oxide matrix, having its interior porous volume substantially filled with said hydrophobic mesh, whereby hydrophobic and amphiphilic molecules with an average molecular mass below 10,000 Daltons are removed.

U.S. Pat. No. 6,783,962 B1 describes a particulate material constructed of a non-porous core and a polymeric base matrix, e.g., dextrane, comprising either chargeable pendant groups or affinity ligands for binding a bio-molecule. The pendant chargeable groups are polyethyleneimine or modified polyethyleneimine and may form a tentacular structure. The material is used to separate bio-macromolecules such as DNA.

WO 2004/073843 discloses a composite material that comprises a support member that has a plurality of pores and a macroporous cross-linked gel filling the pores of the support member.

US 2010/0200507 A1 relates to the purification of a biological sample using a cross-linked polyamine coating immobilized to a membrane.

Most attempts of composite preparation were related to the polymerization of monomers inside the empty space of a support material volume or surface. Such processes may comprise also a covalent attachment of the polymer chains generated to said surface. The present invention is not preferably dealing with polymerization reactions, but depicting the use of precast polymers.

For the synthesis of composite materials comprising the permanent immobilization of precast polymers on a support material basically two ways are available:

- The covalent attachment of the polymer on the surface of the support material
- The immobilization of the polymer on the surface or in the pores via cross-linking.

Covalent attachment is more laborious and costly and will in addition be limited with respect to the layer thickness attached to a surface. On the other hand it is the preferred method if the support surface is flat or inhomogeneous, simply by stability reasons, like it is with membranes, fabrics or tissues.

Cross-linking requires less effort and is applicable with porous materials, because the resultant mesh is nicely trapped and may form a thick layer. On the other hand, there is a significant problem of coating porous particles this way, because they may unintentionally glue together and/or the pores may be clogged.

SUMMARY OF THE INVENTION

In order to attach polymers via cross-linking to the pores of particles or porous monolithic support materials, again two synthetic routes are available:

Precipitating the polymer first, to the inner surface of the support and subsequently cross-linking the precipitated material, by adding the cross-linker dissolved in a solvent which cannot re-dissolve said polymer, followed by initiating the reaction between these components, until the desired degree of cross-linking has been established.

This procedure definitively avoids both pore clogging and particle connections. On the other hand, as shown within the present invention (see Fig. Embodiments 1.1 to 1.4 and Table 2), a different and less favorable morphology is obtained with respect to the accessibility for polymers.

Addition of polymer and cross-linker simultaneously, in order to fill the pores of the support with this mixture, followed by initialization of the reaction between these components. The reaction is continued, until the desired degree of cross-linking is established, thereby mediating the immobilization of the resulting polymer mesh without a need for intermediate physical operations.

Skilled persons would avoid introducing large quantities or volumes of the dissolved precast polymer and the cross-linker simultaneously into the porous support material for reaction, because of danger to plug the pores of the support material, thus resulting in a poor mass transfer of the modified product.

Unexpectedly it has been found, however, that neither clogging nor connection occurred under the synthesis conditions of the present invention. In addition, it is not generally recommended to mix the functional polymer and a reactive cross-linker in advance. Provided that the cross-linking reaction is started at advanced temperature, however, the relating method is preferred, as used in the present invention.

Basically the prior art avoided a "one-step synthesis" of the composite, always performing an intermediate or subsequent drying of the non-finished composite. Moreover, the prior art avoided the presence of any reactive solution outside of the support pore volume. Clogging of support pores with polymer and unintentional connection of particles namely seemed to be an insurmountable problem, which has now been solved by the present invention.

Also therefore an upstream drying before finishing the manufacturing process seemed the best way in order to prevent such a risk in the past.

The concept of avoiding a capture step for the target compound may be defined as a kind of "negative chromatography", characterized in that the majority of undesired compounds is "positively" adsorbed and thus depleted. The strategy to realize this objective is outlined in steps I, II, and III below. It is important to distinguish said "non-binding by exclusion" from any approach where a target compound is only repelled from the adsorbent due to e.g. the same charge of the surface and the molecule. The following threefold discrimination mechanism is the characteristic feature, a strategy enabled with the materials and methods of the present invention:

I. Depletion of substances which exhibit a molecular mass below the molecular mass of the target substance, e.g. the majority of host cell proteins and BSA from a recombinant antibody, where said impurities may originate from host cells and the cell culture media, used in a corresponding fermentation process.

II. Simultaneous depletion of high molecular mass compounds and nano-particles like nucleic acids, viruses and fragments thereof.

III. Recovery of the target compounds, in general molecules which are too big for gaining access to the volume of the mesh pores, e.g. proteins, at the same time avoiding (their strong) binding to the media outer surface.

The object of the present invention is therefore to provide methods and materials enabling purification processes capable to reach the objectives under I, II, and III.

Said "negative" separation step is realized by steric exclusion of target compounds from a particular mesh pore volume, whereas impurities of smaller molecular size enter this volume, where they may be retained, either covalently bound or adsorbed to the inner surface, or distributed towards the mesh volume due to a partitioning mechanism or simply included. Adsorption is preferably achieved by non-covalent interactions, mainly comprising ionic, hydrogen bond, dispersive, van der Waals, and coordinative (ligand exchange, donor-acceptor) forces.

Accordingly, the materials of the present invention are combining in principle the advantages of adsorption, partitioning chromatography and size exclusion chromatography, leaving target compounds excluded, while the impurities are retained inside the polymeric mesh.

Accordingly, the present invention is providing a method for recovering a target compound from a feedstock comprising at least one target compound and at least one impurity, characterized in that a filtrated or a raw feedstock is contacted with at least one polymeric mesh for a sufficient period of time, whereas at least one impurity is retained by the polymeric mesh, subsequently, the polymeric mesh is separated from the purified feedstock containing at least one target compound, and optionally, the at least one target compound is isolated from the feedstock.

In addition, the relatively small contribution of the outer particle surface to the entire particle surface of porous materials significantly facilitates the desired negative adsorption effect, because very little area is left for unwanted adsorption of target compounds to the outer surface.

At the same time the significantly larger inner surface provides high binding capacity for larger amounts of lower molecular size impurities, capable of entering the inner pore volume. Furthermore, certain low concentrated, but highly charged and high molecular mass contaminants, which remain also excluded from the inner pore volume, due to their molecular size, e.g., nucleic acids and virus particles and fragments thereof, may become efficiently captured to the media outer surface, thereby acting as adsorption competitors to the sterically excluded target compounds.

It is important to emphasize that the present invention enables the binding of macromolecules up to a molecular weight of approximately 100,000 Da, equal to a hydrodynamic radius $R_h$ below approximately 5 nm, inside of said polymeric mesh, and not only of small molecules like drugs or drug metabolites. Moreover, the target compound is not bound to the pore volume of the polymeric mesh, but remains excluded. This approach is exactly the opposite of restricted access methods, wherein the unwanted compounds remain unbound and the usually few target substances penetrate the porous space where they are adsorbed.

The purification strategy of the present invention was so far unusual, but implies a valuable way to solve a separation problem in general. As the number of impurities in a raw solution, like plant extract or cell culture supernatant is in the range of up to several thousand moieties, comprising numerous different structures, a very high general affinity has to be provided by the composite material, however, in order to reach depletion levels of >90% in one step. In general, the present invention is providing the teaching of:

Efficient purification processes for macromolecules, characterized in that the target molecule is excluded from the pores of the polymeric mesh of a stationary phase or adsorbent, whereas the major part of impurities is retained by the inner pores. Said inner pores comprise the volumes inside and between the immobilized polymeric coils.

A rapid, easy, inexpensive, and rugged synthesis process for composites, comprising a polymeric mesh, characterized in that a dissolved mixture of a polymer and a cross-linker in a solvent A is added to a support material, generating a nano-porous mesh after reaction and swelling in a solvent B, whereas the volume of the reaction mixture preferably exceeds the pore volume of the suspended support material.

The material design of a polymeric mesh, either soft gels or composites, comprising a cross-linked polymer, characterized in that this mesh is exhibiting a pore size in a particular solvent, specified by the exclusion of valuable molecules which have a hydrodynamic radius of at least $R_{h1}$, whereas at least one undesired compound with a hydrodynamic radius below $R_{h1}$ is retained by the internal pores after penetrating said mesh.

With respect to the present invention, the actually most important field of application is biotechnology. Apart from that, also other polymer purification problems are subject to the present invention.

In bio-separations, e.g., starting from fermentation broths or from body fluids containing target proteins like antibodies, the goal is to deplete substances such as DNA, RNA, host cell proteins (HCP), abundant protective or feed proteins like BSA, transferrin, naturally occurring, or introduced as contents of media for cell growth, and endotoxins, as well as pathogenic germs or fragments thereof. In addition, detergents which are often added in order to achieve better cell growth or conservation should, preferably, be depleted.

Thus the general task in bio-separation is the depletion of the substances as listed under a)-g) below. Actually there are no methods and materials available solving the related separation problems within one or two steps and at a low cost level.

When a fermentation broth (before or after filtration) or a cell culture supernatant (CCS) is used as a feedstock containing the target compound, the target compound is a recombinant protein, preferably an antibody, and the feedstock comprises the following classes of compounds as impurities:

a) DNA, RNA, other nucleic acids, proteins, and organic substances with a molecular mass of at least 100,000 Dalton;

b) host cell proteins (HCP) inclusive proteases with a molecular mass below 100,000 Dalton c) albumin (BSA, HSA, ovalbumin);

d) other proteins present in cell culture media as well as substances of various molecular masses which stem from nutrients or cell metabolism;

e) endotoxins;

f) detergents; and g) germs and microorganisms such as viruses, or fragments thereof.

It is therefore the object of the present invention to provide a purification method, separation materials suitable for this purpose, and a process for the synthesis of said separation material, which exhibit the improvements and advances as given below.

It is the object of the present invention to provide a separation method and purification processes which achieve a simultaneous removal of several impurities, preferably belonging to structurally different classes of substances from a solution (feedstock), whereas at least one target compound remains unbound and is recovered at a high yield.

Unexpectedly it has been found (see Examples), that a polymeric mesh of the present invention is capable to simultaneously remove host cell proteins, nucleic acids, and nutrition proteins at a very high degree, whereas the complex mixture of antibodies from human blood plasma was recovered with high yield.

Thus the present invention relates to the use of a polymeric mesh, either a soft gel or a composite material. Soft gel means a mesh either synthesized from monomers and cross-linkers or preferably synthesized from precast polymers and a cross-linker, thus generating a porous solid material comprising connected polymer chains or coils, which are immobilized by covalent or non-covalent cross-linking.

In one preferred embodiment, in combination with any of the above or below embodiments, the respective soft gel comprises a cross-linked functional polymer, preferably a cross-linked amino group containing polymer and various cross-linkers. In a more preferred embodiment, in combination with any of the above or below embodiments, the composite material is preferably comprising a cross-linked amino group containing polymer immobilized to a porous support material, thus forming a composite.

In a different embodiment, in combination with any of the above or below embodiments, said polymer may be covalently attached to the surface of the support material, and optionally cross-linked in addition.

Both soft gel and composite can be used for the separation of undesired compounds from a solution (feedstock) containing the undesired compounds and a target compound.

The target compounds of the present invention comprise polymers, preferably biopolymers, more preferably proteins, and most preferred antibodies.

The feed solution or suspension comprises at least two dissolved substances of synthetic or natural origin, preferably comprises a fermentation broth, either filtrated (cell culture supernatant) or still containing solid fragments like cells and debris.

An advantageous and improved separation technology should allow:

1. To separate the impurities simultaneously from the purified dissolved target compound at a high degree.

2. To avoid capture of the target compound, because binding on a resin and the subsequent elution contributes to the overall process costs and may also decrease the product yield. Instead of the usual capture procedure, an irreversible or at least strong binding of the majority of impurities is objected.
3. The rapid and inexpensive purification of the target compound from the feed solution or suspension, e.g. from a fermentation broth, by reducing the need for expensive equipment and materials, as well as losses and degradation of the valuable target compounds due to time consuming operations.
4. To preferably avoid a chromatographic step, characterized by a flow through the separation material. In particular, a flow through or perfusion is disadvantageous for the depletion of impurities exhibiting a weaker binding, because they may co-elute with the target compound.
5. To rapidly obtain the clarified solution containing the unbound, purified target compound with a high yield and without adsorbing a significant portion of this valuable compound to the composite material.
6. To preferably dispose the separation material after one cycle without a need of regeneration and thus avoiding the tedious validation of an intended number of process cycles.

The abovementioned technical problems 1-6, preferably the problems 1, 2, and 5, have been solved and the object has been accomplished, according to the present invention providing a method for recovering a target compound from a feedstock comprising at least one compound with a hydrodynamic radius below $R_{h1}$ and at least one target compound with a hydrodynamic radius of $R_{h1}$ or above $R_{h1}$, said method comprising the steps of:

contacting said feedstock with a polymeric mesh comprising at least one amino polymer for a sufficient period of time, whereas the at least one compound with a hydrodynamic radius below $R_{h1}$ is retained by the polymeric mesh, subsequently, separating the polymeric mesh from the purified feedstock containing at least one target compound with a hydrodynamic radius $R_{h1}$ or above, and optionally, isolating the target compound from the feedstock.

$R_{h1}$ is defined as the "exclusion limit" and is ranging between 1 nm and 20 nm, preferably between 3 nm and 10 nm, most preferred between 4 nm and 6 nm.

Isolating means to obtain the purified target compound as a solid or an extract by means of extraction, evaporation, lyophilisation, or other known procedures.

In one preferred embodiment, in combination with any of the above or below embodiments, said polymeric mesh comprises at least one amino polymer.

In particular, according to the present invention, a method is provided for recovering a target protein from a feedstock, either a solution or suspension, comprising at least one target protein and impurities comprising host cell proteins (HCP), DNA, RNA or other nucleic acid, and optionally comprising albumins, endotoxins detergents and microorganisms, or fragments thereof, said method comprising the steps of:
i) contacting said feedstock with a polymeric mesh comprising at least one amino polymer for a sufficient period of time, whereas at least one impurity compound is retained;
ii) subsequently, separating the polymeric mesh from the purified feedstock containing at least one target protein;
iii) optionally, isolating the target protein from the feedstock;

In one preferred embodiment, in combination with any of the above or below embodiments, the target compound is dissolved; in a different embodiment the target compound is at least partly suspended. Also the impurities may be suspended, at least in part.

In one preferred embodiment, in combination with any of the above or below embodiments, the solution or suspension is preferably a filtrated or raw fermentation broth.

The at least one retained compound is a subset of the moieties comprising host cell proteins (HCP), DNA, RNA or other nucleic acid, albumins, endotoxins, detergents, and microorganisms.

In one preferred embodiment, in combination with any of the above or below embodiments, the at least one target compound remaining in the purified feed according to step ii), was excluded from the polymeric mesh volume.

Optionally, within a step iv) the polymeric mesh is washed with a weak solvent, collecting the obtained solution for further processing.

In one preferred embodiment, in combination with any of the above or below embodiments, wherein the amino polymer is either poly(vinylamine) or poly(vinylformamide-co-vinylamine).

In one preferred embodiment, in combination with any of the above or below embodiments, the above feedstock is contacted with a polymeric mesh comprising at least one amino polymer for a sufficient period of time, whereas the at least one impurity compound with a hydrodynamic radius $R_{h2}$ below 4 nm is retained by the amino polymer containing polymeric mesh, and whereas at least one target protein with a hydrodynamic radius $R_{h1}$ of 4 nm or above remains in the purified feed.

By definition the pore volume of the polymeric mesh is considered the particular volume inside the web which is spanned by the immobilized polymeric coils. The outer web surface and the outer surface of a support material do not contribute to this mesh volume.

Retained by the polymeric mesh means the depletion inside of the mesh pores, due to any non-covalent or covalent binding mechanism like adsorption, or due to a partitioning, size exclusion, or extraction mechanism.

In one preferred embodiment, in combination with any of the above or below embodiments, the polymeric mesh comprises a composite material.

Correspondingly, the present invention is providing a method for the synthesis of a composite material for a separation corresponding to step i), wherein a porous support material is filled with a cross-linked functional polymer, preferably with poly(vinylformamide-co-vinylamine), linear or branched poly(vinylamine), poly(allylamine), poly (ethyleneimine), or poly-lysine, or copolymers containing such amino polymers.

Moreover, according to the present invention, the composition of poly(vinylformamide-co-vinylamine) is comprising 5% to 80% of poly(vinylformamide), preferably 10% to 40%, more preferred 10% to 20%.

Moreover, for any contact according to or comparable with step i), the amino polymer containing polymeric mesh is equilibrated in advance to a pH below 8, preferably between pH 3 and 7.5, more preferred between pH 4 and 7, most preferred between pH 6 and 6.8 by mixing with an aqueous buffer or salt solution of preferably a monobasic acid. Said equilibration is also the rule treating soft gels. The buffer or salt concentration in the equilibrated polymeric mesh is below 500 mM, preferably between 10 mM and 200 mM, more preferred between 20 mM and 100 mM. Before using, the equilibrated polymeric mesh is at least wetted with said buffer or salt solution, preferably at least the pore volume is filled.

Preferred monobasic acids are formic, acetic, sulfamic, hydrochloric, perchloric acid, or glycine. Preferred cations are ammonium, alkyl ammonium, sodium, and potassium.

In one preferred embodiment, in combination with any of the above or below embodiments, the salt is ammonium acetate.

Optionally the pH of the feedstock is adjusted to a range between 4 and 7, when the target compound is basic.

The following are preferred embodiments of the method for separating a target compound according to the present invention:

The separation method of the present invention preferably relates to a feedstock, e.g. a fermentation broth, representing either a filtrated solution or a raw suspension, still containing e.g. cells and cell debris.

In a preferred embodiment in combination with any of the above or below embodiments, a solution or suspension comprising recombinant proteins as target compounds, and host cell proteins, DNA, and BSA as impurities is contacted with the amino polymer containing polymeric mesh and the impurities from the feedstock are simultaneously depleted.

In one preferred embodiment, in combination with any of the above or below embodiments, BSA was completely depleted from a 5% (w/v) solution using an amino polymer containing polymeric mesh.

Unexpectedly, it was found that impurities of pI (isoelectric point) values at 7 and above 7 were depleted to at least 95% applying a polymeric mesh of the present invention (Example). It has been shown with a host cell specific ELISA in combination with isoelectric focusing that the majority of said neutral and basic compounds depleted have been host cell proteins (see Methods).

Therefore, in a preferred embodiment, in combination with any of the below embodiments, host cell proteins, exhibiting a pI of or above 7, or exhibit basic properties, capable of ionic interaction, are depleted to 50%, preferably to 80%, most preferably to at least 90%, when using a positively charged polymeric mesh, comprising an amino containing polymer.

Accordingly, the present invention is providing a method for the depletion of compounds with a pI of 7 or above 7, applying an amino group containing positively charged polymeric mesh, preferably a composite, most preferred a composite comprising poly(vinylamine) or poly(vinylformamide-co-vinylamine).

Said polymeric mesh is positively charged after equilibration with a solution of a pH below 8, preferably below 7.

In a preferred embodiment, in combination with any of the below embodiments, target compounds and calibrated test substances which exhibit a hydrodynamic radius $R_{h1}$ above 5 nm, preferably above 4 nm, are sterically excluded from the mesh pore volume under the solvent conditions of use, and thus become separated from other components. Accordingly the present invention is providing a method for the recovery of compounds exhibiting a hydrodynamic radius $R_{h1}$ above 4 nm applying an amino group containing positively charged polymeric mesh, whereas at least 80%, preferably 90% of said compounds remain in the liquid phase.

For the relation between the molecular weight and the hydrodynamic radius see also the section Methods.

In a preferred embodiment, in combination with any of the above or below embodiments, a one step batch adsorption process is used within the procedures of i), ii), and iii) instead of chromatography, characterized in that the purified feed solution is removed by sedimentation or centrifugation from the composite adsorbent, which is loaded with the impurities.

It is emphasized that the batch depletion is operating according to diffusion mechanisms. Preferably no column or other device is applied, which requires a convective transport mechanism, e.g. flow-through.

A skilled person would not expect a satisfactory purification applying only one unit operation, equivalent to any one-theoretical-plate separation step, because there is usually no sufficient selectivity found for complex sample mixtures in such procedure. It is a common doctrine that a successful separation will always require a high plate number in a chromatographic column or selective gradient elution techniques due to a broad distribution of binding constants of the various compounds in the complex feed. With the present invention, however, selectivity towards the various impurities is generated for the high molecular weight target substance by a size exclusion mechanism. The high purification level is therefore enabled by the combination of adsorption and size exclusion mechanism as designed with the materials and methods of the present invention.

In a preferred embodiment, in combination with any of the above or below embodiments, the duration of step i) is 5 to 30 min.

In a preferred embodiment, in combination with any of the above or below embodiments, the efficient depletion of impurities can be reached by a single purification step.

In a further preferred embodiment, in combination with any of the above or below embodiments, the porous support material is a particulate material with an average particle size of 3 µm to 10 mm, preferably between 20 µm and 500 µm, most preferred between 35 µm and 200 µm.

In a preferred embodiment, in combination with any of the above or below embodiments, the target compound is a polymer, preferably a biopolymer, more preferred a protein. Biopolymers are comprising peptides, proteins, glycoproteins, lipoproteins, nucleic acids, and any other compounds once produced by living organisms with a molecular mass above 500 Da.

In a further preferred embodiment, in combination with any of the below embodiments, the protein is an antibody, pegylated antibody or another derivative of an antibody, or an antibody fragment.

Accordingly, the present invention is related to a purification process comprising the steps i), ii), and optionally iii), characterized in that the target compound is an antibody.

Antibody means here any immunoglobulin, of human or other origin, either as recombinant protein from any kind of cell culture or cell free system for protein synthesis, or isolated from biological fluid or tissue.

In one preferred embodiment, in combination with any of the above or below embodiments, it was unexpectedly found that no aggregates were formed from polyclonal antibody (hIgG) mixtures, even after a contact with an amino polymer containing polymeric mesh after 20 min. In contrast, many conventional capture processes suffer from losses in the yield after the non-covalent binding on a resin surface. In addition, a significant portion of the antibody is lost due to aggregate formation during the elution step, even from affinity columns.

DETAILED DESCRIPTION

The combination of the typical essential technical features allows the design of a big number of possible embodiments. Without any claim to comprehensiveness, the following items are considered important embodiments according to the present invention.

In a preferred embodiment, in combination with any of the below embodiments, the undesired compounds are selected from DNA, RNA, albumins, host cell proteins (HCP), endotoxins, detergents, bacteria and viruses. Also fragments of said undesired compounds, like coating proteins, S-layers, cell fragments or debris are within the scope of this embodiment.

In a preferred embodiment, in combination with any of the above or below embodiments, the target compound is an antibody and only the impurities a), b) and c) listed above are depleted from the solution. In a further preferred embodiment in combination with any of the above or below embodiments, the target compound is an antibody and only the impurities a) and b), as listed above are depleted from the solution. In a further preferred embodiment in combination with any of the above or below embodiments, the target compound is an antibody and only DNA and host cell proteins as impurities (undesired compounds) are depleted from the solution.

Preferably, the contaminants or impurities are depleted from a feedstock (e.g. biological fluid, supernatant of a fermentation process, or the fermentation broth before filtration) at a degree of >90%, >95%, >99% of their respective total amounts in the feedstock with concomitant binding of no more than 10%, preferably 5%, more preferably 1% of the total amount of target substances.

Accordingly, the present invention is related to a purification process comprising the steps i), ii), and iii), characterized in that the impurities are depleted to at least 90%, whereas the target protein is recovered to at least 90%.

In a preferred embodiment, in combination with any of the above or below embodiments, the host cell proteins are depleted to an amount of at least 90%, preferably to at least 95%, more preferred to at least 99%.

Accordingly, the present invention is related to a purification process wherein the host cell proteins are depleted from the feed to at least 90% of their initial concentration.

In a preferred embodiment, in combination with any of the above or below embodiments, a certain volume of the particular feedstock (e.g., from a fermentation process before or after removal of the solid materials like a cell culture or its supernatant) is contacted with a sufficient amount of amino polymer containing composite material in suspension. After stirring or shaking for an appropriate time, the composite material is separated from the depleted feed solution by, e.g., aspiration, filtration, or preferably sedimentation or centrifugation.

When the feedstock was a suspension, e.g. containing cells, cell fragments or tissue, these solids are removed together with the composite material. The remaining centrifugate, filtrate or fraction contains the purified target compound.

When using a particulate composite material, some target compound may be remaining within the interstitial volume between the particles. In this case one external void volume of a very weak solvent is applied in order to displace the major portion of the target containing solution. Depending on purity and yield this additional volume may either be combined with the target main fraction, or may be dedicated to another purification step. In the case of antibody purification from a cell culture supernatant, the solvent for displacement may be barely water or a weak buffer far enough away from the target protein, preferably antibody pI.

Weak solvents or weak buffers exhibit preferably no chromatographic elution power, and are characterized in that the solubility for the majority of the impurity compounds of the feed is low.

In a preferred embodiment, in combination with any of the above or below embodiments, the ratio of feedstock to composite material is in a range between 5 and 100 liter per kg and the preferred contact time is 5 to 60 min.

As long as the target compounds remain unbound in the liquid phase to an acceptable degree, the subsequent elution of bound substances is usually not required, because the composite materials will be preferably disposed at the end of the process cycle, i.e., they are designed for single use. The elution and isolation of any bound compounds is, however, still within the scope of the present invention and can be achieved by applying any known elution methods.

In order to fulfill the stringent quality requirements in place for APIs (active pharmaceutical ingredients), the target compound purified according to the new technical lore may require one or two additional purification steps. This may be the case if depletion below the detection limit is necessary, or if a complex heterogeneous class of side products or impurities, like host cell proteins, must be removed to a level below 10 ppm, based on the mass of the final API.

The use of any polymeric mesh of any of the below or above embodiments in a sequence with any other purification steps, is therefore subject to the present invention. In combination with any of the above or below embodiments, their use either before or after an ion exchanger or affinity chromatography step, or any other purification steps is within the scope of the present invention, particularly if affinity based separation steps, e.g. selective adsorption of target compounds to any kind of separation media harboring protein A, protein G, or a combination of both is considered. In addition, any combination with membrane filtration, depth filtration or applying a monolithic separation agent, is considered within the scope of the present invention. In a more preferred embodiment, in combination with any of the above or below embodiments, the polymeric mesh is used before or after an ion exchanger or affinity chromatography step, or other purification steps.

Accordingly, the present invention is related to a combination with one or more additional separation steps, characterized in that the above steps i), ii), and iii) are carried out with the raw feed suspension or solution, in advance to any further chromatographic or non-chromatographic purification step.

Although the target compound is excluded from the polymeric mesh, a small amount may be adsorbed to its outer surface. In order to achieve a sufficient yield or/and recovery rate of the target compound, it is necessary to avoid the binding of a significant amount of this target compound to the external surface of a polymeric mesh. Due to the inevitable distribution in the pore diameters of the polymeric mesh and due to potential interaction with the external surface, it is often impossible to entirely avoid losses of small amounts of the target substance. As these losses may reduce the overall recovery rate of valuable substances, additional strategies have been combined within the present invention to minimize such losses.

Together with the exclusion effect provided by the specific porosity of the polymeric mesh, the invention thus employs also the following general design principles:

A1. For applications in an aqueous environment, the polymer portion, which is in contact with the mobile phase, should be polar, close to the polarity and/or charge of the target compound. Consequently, the solvated target compound is distantly separated from the composite material and does not bind thereto.

A2. Accordingly, in organic solvents lipophilic targets are repelled by a hydrophilic polymer, and vice versa.

B1. When the polymer bears a charge, the pH of the binding buffer amounts to +/−1 unit below or above the isoelectric point (pI) of the target compound, provided it is an ionic species, in order to keep the molecule almost uncharged.

B2. More preferably the polymeric mesh is equilibrated with a buffer or solvent, adjusted to a pH of +/−1 unit below or above the isoelectric point (pI) of the target protein, most preferably a pH, where the binding of the target compound is minimized, prior to contacting it with the feed.

Preferably within contact times below 20 min., the pH-conditions of the preliminary mesh equilibration remain sufficiently unchanged, in order to avoid said undesired interaction with the target compound.

C. High salt concentration (preferably >100 mM NaCl equivalents or conductivities>10 mS/cm) reduces polar binding forces (mainly ionic charge interaction on the outer surface of the polymeric mesh), and thus the target compound is less attracted. Nevertheless, the strong, e.g., multivalent binding forces inside the polymeric mesh are capable of adsorbing incoming molecules also at high salt load.

D. The multivalent strong binding of large macromolecular chain molecules like small quantities of DNA from a fermentation process on the external surface will hinder or suppress the binding of a target molecule by competitive displacement, as long as it is not interacting with the DNA itself.

The use of the polymeric mesh of the present invention therefore comprises a preliminary step of rinsing and equilibrating the polymeric mesh with a solvent or buffer, adjusted to a pH and ionic strength, such as to avoid or minimize the binding of the target compound, or preferably with a solvent of lower elution strength compared to the solvent of the feedstock. This measure improves also the binding of the impurities, exhibiting lower binding constants.

In combination with any of the above or below embodiments, steps i), ii), and optionally iii) of the present invention are accordingly combined with one or more measures under A., B., C, or D. above.

"Target compound" refers to any substance of value, subject to a purification according to the present invention.

It is also the objective of the present invention to provide a method for the preparation of a inexpensive composite material. Said composite material is enabling various substance separation or purification methods, e.g., a simultaneous removal of several structurally different classes of substances from a solution (feedstock).

Said objective is achieved by a process, comprising:

Filling at least the pore volume of a porous support material with a solution of at least one functional polymer or co-polymer and at least one cross-linking agent (reaction mixture), and in situ immobilizing said functional polymer by cross-linking, whereas the support material is particulate, pellicular or monolithic.

Pellicular means that a solid particle or material is coated with a porous layer.

Monolithic means a homogeneously porous piece of support material exhibiting a thickness of at least 0.5 mm.

In a preferred embodiment, in combination with any of the below embodiments the pores are filled with a mixture of the functional polymer and the cross-linker, and reacted in a one step process without preliminary or intermediate drying, Within another embodiment, in combination with any of the below embodiments, after filling the pores, the solvent may be completely or partially removed before the cross-linking reaction is started. When using epoxide cross-linkers or cross-linkers which do not react at ambient temperature, this solvent reduction is preferably achieved by evaporation at temperatures below 30° C. When the desired portion of the solvent is removed, the cross-linking reaction starts at temperatures at or above 50° C. Within another embodiment, in combination with any of the below embodiments, after the partial or complete removal of this solvent, the empty space may be filled partially or completely with a different solvent.

In all these above cases the cross-linker was already present during the initial pore filling step and the reaction are performed inside of or at the interface of the porous support.

Provided that the support material is particulate or an assembly of monolithic items, e.g. a stack, said process is alternatively comprising:

Filling at least the sedimentation volume (see Methods) of the support material (pore volume and the interstitial volume between the particles or layers) with said reaction mixture; or optionally applying an excess reaction mixture of up to 120% of said sedimentation volume containing the reaction mixture.

In a preferred embodiment, in combination with any of the below embodiments, the support material is filled with the reaction solution applying the spontaneous soaking of the liquid into the pores. Any other method of pore filling known from the prior art is also applicable.

Using soaking techniques, it is difficult to fill exactly the entire pore volume of porous particle support materials, however. As also the pore volume determination (compare Methods) will always imply a certain error, it becomes even more difficult to accurately determine the necessary volume of reaction liquid to be applied. Therefore one can hardly avoid that a significant fraction of the particles will become slightly overloaded with liquid on the outer surface, e.g. simply because of the surface tension of the liquid. As a consequence, pore portions of other particles inevitably will not be completely filled, when only a volume of the reaction mixture is added, which is equal to the pore volume determined.

As it is basically impossible during the manufacturing process to contact the particles all at once with the liquid, this problem of inhomogeneous particle filling will even become more severe, in particular while treating large quantities.

With respect to the dedicated applications, it is the absolute request to completely cover the accessible surface of a support material with the cross-linked polymer Thus the abovementioned kind and extent of inaccuracy is not negligible. Support surface fractions which are not covered with polymer will have a negative impact on the selectivity and mainly recovery during a separation process. There may be a stronger adsorption of the target compound on these spots, in particular with protein targets compounds on polar support materials like silica or other polar media.

Said problems can be avoided applying a sufficient excess of reaction mixture volumes, enabling the complete wetting and polymer coverage of the entire support surface. In this case, however, it will be necessary to prevent any cross-linking reactions outside of the particle volume. Moreover, also no rapid reaction of the polymer and the cross-linker is acceptable during a sufficient pot life time after the preparation of the reaction mix.

Surprisingly it has been found that even when the interstitial volume between particles partially or completely contains the reaction solution, not any particles are fused together. Without being restricted to any explanations, the cross-linker is probably adsorbed by the porous support material in this case (Example 1). Accordingly the composite preparation is not negatively affected if a certain excess of polymer cross-linker solution is applied. These unexpected findings allow a simplification of the manufacturing process according to the present invention, especially while producing large quantities of composite material, because the reaction preferably will be carried out with the sedimented support material without stirring, shaking, or other movement.

In combination with any of the above or below embodiments, at least the pore volume of a support material is filled with the reaction solution, preferably an excess solution related to the pore volume, more preferred the sedimentation volume, and most preferred a slight excess of the sedimentation volume are added. Therefore, in combination with any of the above or below embodiments, a solution of the functional polymer, preferably of poly(vinylamine) or poly(vinylformamide-co-vinylamine), together with a bis-epoxide, preferably ethyleneglycol-, propyleneglycol-, butanediol-, or hexanedioldiglycidylether, is offered in amounts of at least the pore volume, preferably of the sedimentation volume, and most preferred between 110% and 120% of the overall sedimentation volume, whereas the pores of the support material became completely filled. Unexpectedly at the end of the reaction neither polymer gel was formed outside of the pores nor did the particles glue together.

In a preferred embodiment, also in combination with any of the above or below embodiments, an excess of the cross-linker containing solution of a functional polymer, preferably between 110% and 120% of the support material sedimentation volume is added, so that the interstitial volume between the particles is completely filled with liquid, and a thin liquid film of reaction solution covers the top of the sedimented solids.

In a more preferred embodiment, in combination with any of the above or below embodiments, the cross-linker is applied in water or in an aqueous solution together with the cross-linkable polymer. Although even cross-linker quantities below 2% (v/v), preferably using the abovementioned bis-epoxides, most preferred hexanediol diglycidylether are not completely soluble in water, the emulsion formed surprisingly distributes inside the support material pores, thus generating a stabile cross-linked polymeric mesh.

It is advantageous for the synthesis process and the subsequent wash and equilibration to use only aqueous media.

For the purpose of reaction including preliminary pore filling, the cross-linkable polymer or co-polymer is preferably dissolved in a solvent or buffer which will shrink the polymer. Thus the molecular volume of the individual polymer coils or bodies will be minimized, allowing introducing a maximal amount of polymer into the narrow pores.

In the case of polyacrylates, or other acidic polymers swelling is suppressed within the acidic pH range, generating a non-dissociated configuration. In the case of amino containing polymers a basic pH generates this desired molecular shrinking. Neutral polymers, like polyvinyl alcohol, are preferably dissolved in aqueous mixtures close to the theta point, e.g., with water-propanol mixture.

In a preferred embodiment, in combination with any of the below embodiments, the present invention is accordingly related to pore filling steps with a reaction solution prepared with a non-swelling solvent, solvent mixture or buffer.

In a preferred embodiment, in combination with any of the below embodiments the reaction mixture is comprising the functional polymer or co-polymer, the cross-linker and optionally auxiliary substances like buffering compounds, salts, or various side products, which stem from the raw reactants applied, altogether dissolved, suspended or emulsified in a solvent or solvent mixture.

The present invention also provides a polymeric mesh comprising a cross-linked precast polymer exhibiting a pore size distribution in a particular solvent or buffer, characterized in that the upper pore size limit of the fully swollen polymer mesh is defined by the exclusion of a polymeric standard molecule with a hydrodynamic radius $R_{h1}$ (nm), whereas a pre-selected, defined fraction of the overall pore volume remains accessible for polymeric standard molecules with a hydrodynamic radius between $R_{h1}$ and $R_{h2}$ with $R_{h1} > R_{h2}$.

Preferred polymeric standard molecules for the application in aqueous solution are polyethylenoxides, dextranes, and pullulanes.

Said polymeric mesh is capable to retain at least one of the penetrating substances inside the accessible pore volume in combination with any of the above or below embodiments.

Said exclusion properties are not limited to a composite design, but are also subject to soft gel embodiments.

Preferred values of $R_{h1}$ are 5 nm, more preferred 4 nm. The preferred value of $R_{h2}$ is 2 nm, more preferred is 1 nm, most preferred is 0.2 nm.

A preferred range with the limits of $R_{h1}$ and $R_{h2}$ is between 1.5 nm and 5 nm, because this range of pore sizes is basically accessible for proteins with a molecular weight between 10,000 Da and 100,000 Da.

The following are preferred embodiments of the preparation of said polymeric mesh according to the present invention:

Co-polymers, polycondensation products (e.g., polyamides), and oligomers or molecules with at least four equal or different repetitive units are considered within the polymer definition for the present invention.

In a preferred embodiment, in combination with any of the below embodiments, the individual cross-linkable polymer or co-polymer chain is comprising at least one functional group (a "functional polymer").

Basically the functional polymer may be any kind of polymer comprising at least one or more identical or different functional groups.

Preferably the functional polymer is bearing at least one OH—, SH—, COOH—, $SO_3H$, or amino group.

Preferred hydroxyl containing functional polymers are poly(vinylalcohol), agarose, and cellulose. Preferred carboxyl containing polymers are poly(acrylate) or poly(methacrylate).

If the immobilized polymer or copolymer is functionalized, it exhibits at least one cross-linkable group per molecule.

In a preferred embodiment, in combination with any of the above or below embodiments, the functional polymer is an amino group containing polymer, or an oligomer with at least four amino groups, more preferred a polyamine. Amino groups are primary and secondary.

Amino group containing derivatives of polymers, e.g. a polyvinylalcohol or a polysaccharide bearing amino groups, are within the scope of the present invention.

In a further preferred embodiment, in combination with any of the above or below embodiments, the polyamine is a poly(vinylamine) or poly(vinylformamide-co-vinylamine).

In a further preferred embodiment, in combination with any of the above or below embodiments, the functional polymer is soluble in water.

In a further preferred embodiment, in combination with any of the above or below embodiments, the reaction compounds are soluble in water, or are at least emulsified.

It is another object of the present invention to provide an efficient general synthesis procedure for composite materials, comprising only one operational step at moderate temperature without a need of pre-treating, e.g. purifying any of the starting materials or intermediates.

In addition, in the most preferred embodiment the synthesis and the washing and equilibration of said composite material avoids the utilization of organic solvents.

One-step and in situ means, that all reactants are mixed, reacted, and the composite is washed within one working operation, in order to obtain the desired product. Mainly the immobilization via cross-linking is achieved at once with or after the application of the complete reaction mixture.

In particular, there is no drying step applied before the cross-linker is added.

In a preferred embodiment, in combination with any of the below embodiments, the cross-linking reaction is not started already during the pore filling, but subsequently, preferably at elevated temperature or with a pH shift. The cross-linking with epoxide cross-linkers is thus started at temperatures preferably above 50° C., while at room temperature no visible gelation occurs after 30 minutes, even not after two hours.

The cross-linking of amino containing polymers with reactive cross-linkers like carbonyldiimidazole is suppressed at pH values below 7, preferably below 6, and will be started after adjusting the pH above preferably 7, more preferably 8, because the reaction velocity of the protonated amino groups is very low. Within another embodiment, in combination with any of the below embodiments, the cross-linker is applied first into the support material pores, optionally the resin is at least partially dried, and finally the polymer solution is introduced and cross-linked.

The present invention is also providing a process for the preparation of a composite material comprising:

Filling at least the pore volume of a porous support material with a solution of at least one functional polymer or co-polymer and at least one cross-linking agent (reaction mixture), and immobilizing said functional polymer by cross-linking, whereas the reaction mixture is containing salt, buffer and/or other compounds, which are not incorporated in the composite products.

In a preferred embodiment, in combination with any of the above or below embodiments, a raw polymer or polymer solution and a cross-linker of industrial quality are used for this composite synthesis, still containing the salts and other side products from the manufacturing process of the respective reagent.

Unexpectedly, it has been found that any side-products, mainly salt or impurities are not disturbing the reproducible cross-linking process. Together with un-reacted, e.g., excess compounds, they are removed from the composite by the subsequent washing steps after the simultaneous immobilization of the reactants. This kind of processing saves the overall effort and costs for concentrating or cleaning the reactive compounds in advance. Therefore, cheap industrial quality polymers and cross-linkers can be used instead of expensive high purity grade chemicals.

Within a preferred embodiment, in combination with any of the below embodiments, raw polyamines are used for the composite synthesis, more preferred, a raw poly(vinylamine) or poly(vinylformamide-co-vinylamine) solution is used, containing the salts, sodium hydroxide, sodium formate, and other side products from the polymer manufacturing process (Example 1).

Preferred are support materials having an average pore size of 10 nm to 5 mm, more preferred are pore sizes between 20 nm and 500 nm, most preferred is the range between 20 nm and 100 nm.

The form of the porous support material is not particularly limited and can be, for example, a membrane, a non-woven tissue, a monolithic or a particulate material. Particulate and monolithic porous materials are preferred as the support. Pellicular materials are also within the scope of the present invention. The shape of the particulate porous support material can be either irregular or spherical. In combination with any of the above or below embodiments, the porous support material preferably has a substantially irregular shape.

In a further preferred embodiment, in combination with any of the above or below embodiments, the porous support material is a monolithic or a particulate material.

In a further preferred embodiment, in combination with any of the above or below embodiments, the porous support materials are composed of a metal oxide, a semi-metal oxide, ceramic materials, zeolites, or natural or synthetic polymeric materials.

In a further preferred embodiment, in combination with any of the above or below embodiments, the porous support material is porous silica gel.

In a further preferred embodiment, in combination with any of the above or below embodiments, the porous support material is porous cellulose, chitosane or agarose.

In a further preferred embodiment, in combination with any of the above or below embodiments, the porous support material is porous polyacrylate, polymethacrylate, polyetherketone, polyalkylether, polyarylether, polyvinylalcohol, or polystyrene.

In a further preferred embodiment, in combination with any of the above or below embodiments, the porous support material is a particulate material with an average particle size of 1 to 500 µm.

In a further preferred embodiment, in combination with any of the above or below embodiments, the monolithic support material is a disk, a torus, a cylinder or a hollow cylinder, with at least 0.5 mm height and with an arbitrary diameter.

In a further preferred embodiment, in combination with any of the above or below embodiments, the support material is silica, alumina or titanium dioxide with an average pore size (diameter) between 20 nm and 100 nm (as analyzed by mercury intrusion according to DIN 66133) and a surface area of at least 100 m$^2$/g (BET-surface area according to DIN 66132).

In a further preferred embodiment, in combination with any of the above or below embodiments, the support material is irregularly shaped silica, alumina or titanium dioxide, with a surface area at least 150 m$^2$/g.

Even more preferred are irregularly shaped silica gel materials, exhibiting an average pore diameter of 20-30 nm, which are allowing the access of polymeric pullulane standards with a hydrodynamic radius $R_h$ below or equal to 6 nm, when dissolved and measured under iSEC conditions (see FIG. 1 consisting of Fig. Embodiments 1.1, 1.2, 1.3 and 1.4) in 20 mM ammonium acetate at pH 6.

Most preferred is irregular silica with a BET surface area of at least 150 m$^2$/g, preferably 250 m$^2$/g and a pore volume (mercury intrusion) of at least 1.5 ml/g, preferably 1.8 ml/g. The use of silica and silica derivatives for preparative protein purification purposes is uncommon, and average pore sizes of more than 50 nm are the preferred range in the prior art, usually achieved with organic support materials.

Inorganic support materials are available also in a dry state, enabling the introduction of the dissolved reagents by simply filling the pores, without an initial drying and polymer purification step.

In the most preferred embodiment, in combination with any of the above or below embodiments, the pores of silica gel with 25 nm mean pore diameter, preferably of the support material Davisil 250, are filled with an aqueous solution containing a mixture of a bis-epoxide cross-linker and polyvinylamine Lupamin 50/95 (average molecular weight 50.000 Da., hydrolysed to roughly 95%) or Lupamin 45/70 (average molecular weight 45.000 Da., hydrolyzed to about 70%), or materials with equal specification, at a pH between 9 and 11, and reacted at a temperature of 50-60° C. for 24 to 48 hours.

Accordingly is the present invention related to a process for the synthesis of a composite material comprising a porous support material and an amino group containing polymer, characterized in that the support material is silica gel with a mean pore diameter between 20 nm and 100 nm and the pores are filled with a mixture of the amino group containing polymer and the cross-linker, and reacted in a one step process. preferably without preliminary or intermediate drying, thus immobilizing the amino group containing polymer by cross-linking.

If (functional) polymers are immobilized inside the pores of a support material, they do not display any observable mesh porosity in a dry state. After drying such a composite, approximately the pore size distribution of the basic support material is found again, using the established methods like BET nitrogen adsorption or mercury intrusion porosimetry, at least as long as the degree of cross-linking remains below 25%. This behaviour may be attributed to the strong adhesive forces inside the polymer coils, causing shrinkage of the mesh to values close to the excluded polymer volume. If the functional groups are bearing a charge as it is, e.g., with polyacrylate or polyamine, the resultant excluded volume may be slightly bigger.

If wetted by a solvent or in a suspension the polymer structure displays a fundamentally different morphology. Provided sufficient solvation, the polymer mesh swells until reaching the maximal possible volume, spanning a classical hydrogel structure. In this case, the resultant porosity of the polymeric mesh is dependent on the nature of the solvent (polarity, etc.), the pH, ionic strength and the concentration of auxiliaries like detergents.

When treating functional polymers, in particular charged polymers, according to the present invention, it is important to distinguish between the degree of filling the support material pores whilst the process of immobilization of the polymer, and "filled or occupied pores" whilst the use of the composite in separations.

In the first case of polymer attachment, the entire support pore volume is filled with a solution of the reagents. In the latter cases the mesh pores are full, i.e. not accessible any more for molecules of a certain hydrodynamic radius $R_{h1}$, due to the swelling behavior of the cross-linked polymers and the resultant mesh in the selected solvent. In each particular case the potential swelling behavior can be estimated from the available polymer literature. Thus the degree of pore filling can be realized, adjusted and controlled by the selection of the appropriate solvent and pH.

Appropriate solvent means a solvent which is capable to swell the polymeric mesh, according to the rules of polymer solvation, as known to a skilled person. For details see H.-G. Elias, Makromoleküle, Hüthig & Wepf, Basel, Bd. 1 (1990), p. 145-207.

With composite materials, but also with pressure stabile polymer gels of the present invention iSEC is the method to determine pore volumes and pore volume fractions. Protocols as mercury intrusion or BET-nitrogen adsorption, as used for rigid porous materials are not applicable here, because the mesh will collapse after drying.

In a preferred embodiment, in combination with any of the below embodiments, an amino group containing polymer is introduced into the support material in a shrunk state, preferably above pH 8.5, more preferably between 9 and 12, most preferred between 10 and 11, thus allowing a maximal density of the dissolved polymer under the conditions of pore filling. After cross-linking and swelling at a pH below 8, the space occupied by the polymeric mesh inside the initial support pore volume will increase and finally be maximized at an acidic pH.

In a preferred embodiment, in combination with any of the below embodiments, the object of the present invention is reached by the reaction of at least one shrunk cross-linkable polymer with at least one cross-linker, thus forming a mesh, which is selectively swollen or shrunk in certain solvents or buffers.

Under the conditions of use the degree of pore filling can be adjusted to a desired level by choosing appropriate solvents or solvent mixtures. By definition, the pores of a polymeric mesh are considered full, if a standard molecule with a selected and well-defined hydrodynamic radius $R_{h1}$ cannot enter the mesh pores any more. In the present invention, this degree of swelling is calibrated and adapted using the methods of inverse size exclusion chromatography (iSEC) as outlined in the section Methods and as demonstrated with FIG. 1 (Fig. Embodiments 1.1 to 1.4) and further controlled during the purification process, while maintaining the corresponding swelling state by the presence of the selected buffers.

Basically the steric exclusion of molecules with a defined minimum ("or critical") hydrodynamic radius takes place from a particular pore volume fraction, as demonstrated by comparison with the pullulane molecular mass standards, used as model target compounds, according to Fig. Embodiments 1.1 to 1.4 and Examples.

With the poly(vinylamine) or poly(vinylformamide-co-vinylamine) containing composites of the Examples, the degree of swelling is adjusted, using a 20 mM-200 mM solution of ammonium acetate. For the subsequent depletion of impurities the composite is equilibrated with preferably 50 mM ammonium acetate buffer at a pH below 7, more preferably between 3 and 7.

Therefore, in a preferred embodiment, and in combination with any of the above or below embodiments, the degree of polymer swelling is determined by inverse Size Exclusion Chromatography, utilizing a selection of polymer standards of well-defined molecular size for calibration and concomitant adjustment of the polymeric mesh by adding the appropriate solvents or solvent mixtures.

According to the present invention, the accessible mesh pore volume increases under swelling conditions and decreases under shrinking conditions in appropriate solvents. The mesh pore size volume and the mesh size distribution is always related to the space inside or between the particular connected polymer coils or globules, and not to the space initially available or finally remaining in the support material.

The amount of polymer introduced into the support material and immobilized is preferably controlled by the polymer concentration in the respective reaction solution.

The degree of support pore filling and the mesh size distribution under application conditions, in contrast, is controlled by the solvent-dependent swelling of the polymer and its total immobilized amount. Both parameters taken together, the overall amount of polymer immobilized and the degree of swelling allow adjusting the percentage of the overall pore volume which is filled with the polymer.

In a further preferred embodiment, in combination with any of the above or below embodiments, the degree of support pore filling and the mesh size distribution under application conditions is achieved and determined by introduction and immobilization of different polymer amounts and by the subsequent measurement of the pore size distribution. The amount of polymer to be immobilized is preferably adjusted by the polymer concentration in the reaction solution. Hence, the maximal possible polymer amount, which can be immobilized, is easily elucidated for said purpose.

The degree of filling is exactly determined and standardized by weighing the wet and dry materials before and after introduction of the polymer-cross-linker solution.

For the separation or purification of dissolved target polymers, e.g., proteins, it is moreover advantageous to achieve the retention of various impurities simultaneously with the steric exclusion of at least one target compound.

In combination with any of the above or below embodiments, the present invention is providing materials and methods for the use of the polymeric mesh, preferably of a composite material which achieve a simultaneous removal of several structurally different classes of substances from a solution, preferably a feedstock, whereas at least one target compound remains substantially unbound and is recovered at a high yield. This target compound yield is preferably 80%, more preferably 90%, and most preferred above 95%.

The above and the following further objects of the present invention are also achieved according to the embodiments as outlined below.

In combination with any of the above or below embodiments, the present invention is providing methods for the synthesis and the use of a polymeric mesh exhibiting an upper, but variable pore size $R_{hi}$, when equilibrated with an appropriate solvent, thus capable of retaining a significant amount of compounds with a hydrodynamic radius below this exclusion limit $R_{hi}$ (nm) inside the pore volume, preferably 50%, more preferred 80%, most preferred>90% of the initial content, whereas the pores of the polymeric mesh are not accessible for the at least one target compound with a hydrodynamic radius of $R_{hi}$ or above $R_{hi}$ and thus allows to recover said target compound in the solution, preferably in the purified feed. According to the solvent dependent swelling of the mesh, this exclusion limit $R_{hi}$ is a variable size. The main parameters controlling $R_{hi}$, except of solvent strength and pH, are the structure of the functional polymer, the nature of the cross-linker, the degree of cross-linking, and, in the case of composites, the pore size distribution of the support material.

The term $R_{hi}$ indicates that a series of different sizes will be obtained as the function of the swelling degree. In contrast, are $R_{h1}$ and $R_{h2}$ expressing fix distances in a particular application case.

Said object of combining sorption, partitioning, and size exclusion is preferably achieved by the use of a composite material comprising:

a porous support material having an average pore size between 5 nm and 5 mm, wherein the overall pore volume of the porous support material is filled with a polymer, which is cross-linked and thus forming a mesh, which is excluding standard molecules of a hydrodynamic radius $R_{h1}$ (nm) and thus provides an exclusion limit for synthetic and natural macromolecules with a hydrodynamic radius of $R_{h1}$ or above $R_{h1}$ (nm), when equilibrated with an appropriate solvent.

Provided that the target compound is an antibody, said exclusion effect is achieved if this mesh is inaccessible for molecules exhibiting a hydrodynamic radius $R_{h1}$ above 5 nm, preferably above 4 nm.

Also in combination with any of the above or below embodiments, the present invention provides the synthesis and use of soft gels or composite materials exhibiting a defined mesh pore volume, capable of retaining a significant amount of compounds with a hydrodynamic radius $R_h$ below 4 nm, preferably 50%, more preferred 80%, most preferred>90% of the initial content, while this fraction of the pore volume is inaccessible for antibodies.

Pore volume in the context of the present invention means the integral or sum of the entire particular pore volume fractions, each of which fractions is defined by a lower and an upper pore size.

Also in combination with any of the above or below embodiments, the present invention is providing the synthesis and use of soft gels or composite materials exhibiting a defined pore size distribution, capable of retaining a significant amount of compounds with a hydrodynamic radius $R_{h2}$ below 4 nm within their mesh pore volume, preferably 50%, more preferred 80%, most preferred>90% of the initial content, whereas this fraction of the pore volume is inaccessible for target compounds with $R_{h1}$ at or above 4 nm, like antibodies, and whereas another portion of undesired products with higher molecular weight is bound to the external surface.

The above-mentioned another undesired products are preferably nucleic acids and/or host cell proteins with a molecular weight above 100,000 Da.

The above objects of protein purification are preferably achieved by the use of a composite material comprising:

a porous support material having an average pore size of 20 nm to 5 mm, wherein, under the conditions of application at a pH below 8, the overall pore volume of the porous support material is filled with a cross-linked amino group containing polymer, said composite material is characterized by a pore size distribution, wherein molecules with a hydrodynamic radius $R_h$ of 4 nm and above, in particular the calibrated pullulane standard with a molecular weight of 21.7 kDa and $R_h$=3.98 nm, are excluded from at least 90% of the pore volume, and wherein at least 35% of the overall pore volume is represented by pores which are accessible to a pullulane standard 6.2 kD with a hydrodynamic radius $R_h$=2.13 nm.

Optionally, at least 15% of the overall pore volume of the above composite material may be represented by pores which are accessible to a pullulane standard 10.0 kDa with a hydrodynamic radius=2.7 nm.

In combination with any of the above or below embodiments, the above amino group containing polymer is preferably comprising poly(vinylamine) or poly(vinylformamide-co-vinyl amine).

These enhanced pore volume fractions of 35% and 15% respectively, are advantageous, in order to provide significant binding capacity for, e.g., proteins with a molecular mass between approximately 10,000 Da and 100,000 Da, basically representing molecular hydrodynamic radii $R_h$ between approximately 2 nm and 4 nm in the selected solvent or buffer.

In combination with any of the above or below embodiments, the present invention provides the use of a suspended polymeric mesh, comprising poly(vinylamine) or poly(vinylformamide-co-vinylamine) and a cross-linker, characterized in that pullulane standards exhibiting a hydrodynamic radius above $R_h=3.98$ nm are substantially excluded from the pore volume, thus defining the upper pore diameter in the respective solvent, whereas the mesh volume is accessible to a pullulane standard 6.2 kD with a hydrodynamic radius $R_{h2}=2.13$ nm.

Substantially means that at least 90% of the pore volume is not accessible.

A polymeric mesh comprising amino polymers is preferably obtained by cross-linking the respective polymer in aqueous solution, whereas the pH is between 8 and 13, preferably between 9 and 12, most preferred between 10 and 11.

Figure 1A:
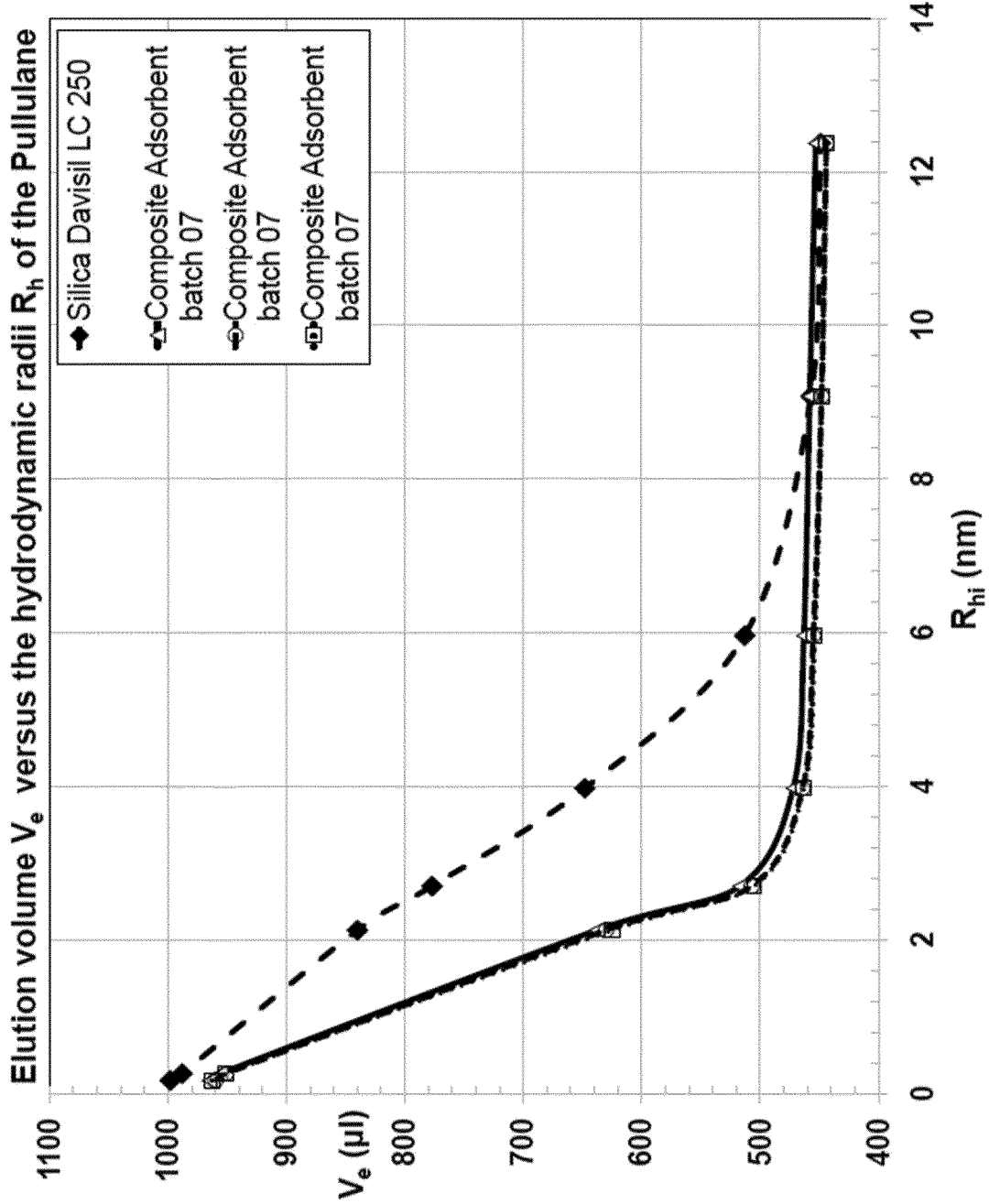
Figure 1:
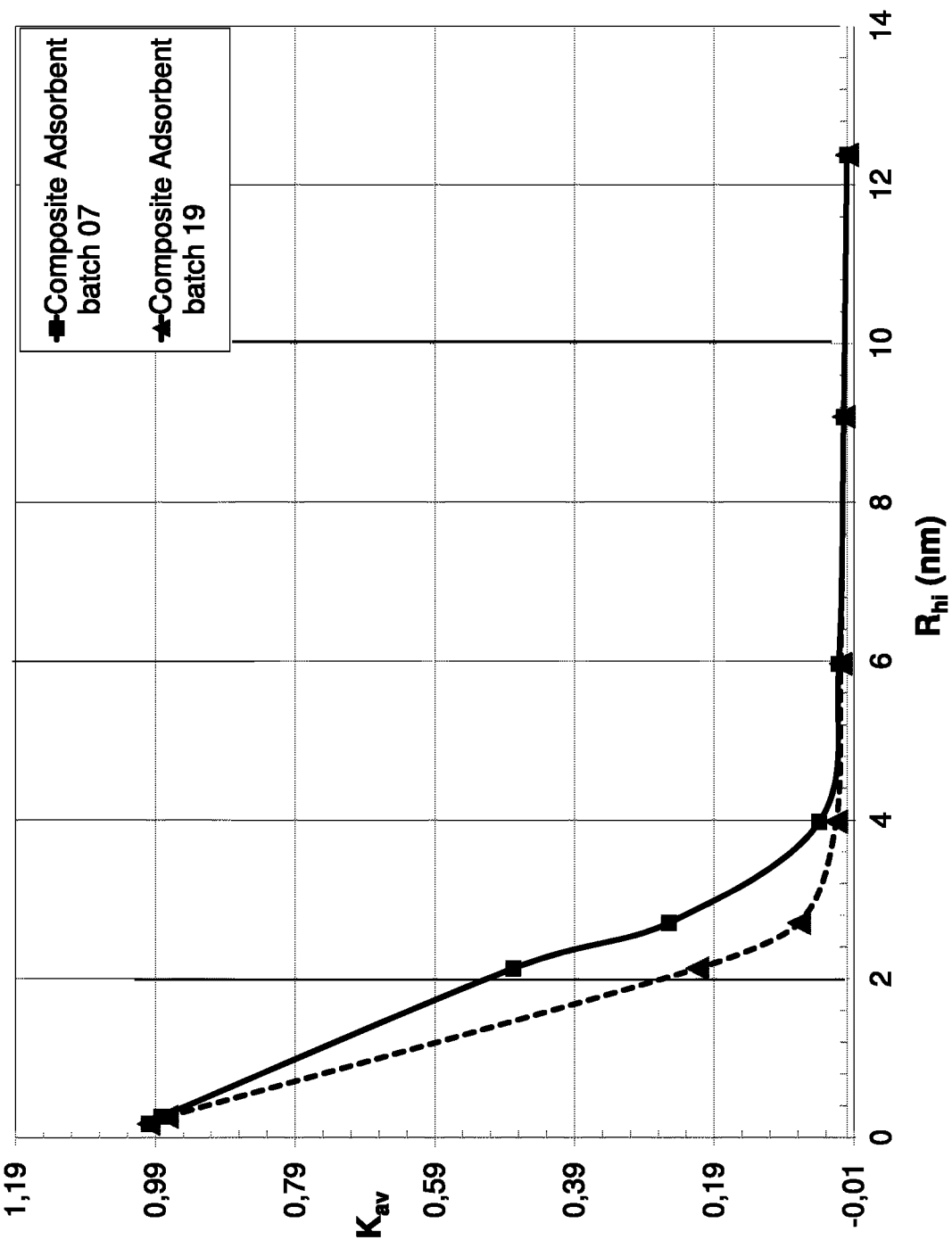

The pore accessibility and the exclusion limit are always determined by iSEC using pullulane standards in 20 mM ammonium acetate buffer at pH 6 (see FIG. 1 and Methods).

The feed solution comprises mixtures of synthetic or natural origin. Preferably the feed is a fermentation broth, either filtrated (cell culture supernatant) or crude, still containing solids like cells and cell debris.

In combination with any of the above or below embodiments, the average molecular weight of the functional polymer is preferably 2,000 to 2,000,000 Dalton, more preferably 10,000 to 1,000,000 Dalton, even more preferably 15,000 to 200,000 Dalton, most preferably 20,000 to 100,000 Dalton.

In combination with any of the above or below embodiments, any cross-linker known from prior art is applicable for the immobilization of a polymer according to the present invention.

In combination with any of the above or below embodiments, the cross-linker is preferably a bis-oxirane or a bis-aldehyde such as succinic or glutaric dialdehyde, as long as the polymer is harboring amino groups. If a bis-aldehyde is used as the cross-linker, a subsequent reduction step is advantageous for stabilisation purposes.

Cross-linkers with more than two reactive groups are also applicable.

Preferably the cross-linker should represent the chemically activated reagent in the formation of the polymeric mesh.

Alternatively, the polymer may be introduced as the chemically activated partner, using the reagents and procedures as known from the prior art, in particular from peptide synthesis.

The polymer may also a priori be reactive. In this case functional groups of the polymer may be generated during the cross-linking process itself or subsequently, applying reactive or activated polymers, e.g., anhydrides from poly(maleic acid), or poly-oxiranes.

Both, cross-linker or polymer may also be activated using the prior art carbodiimide reagents, preferably the water soluble carbodiimides, in order to allow the whole reaction to take place under non-aqueous conditions.

In combination with any of the above or below embodiments, acrylic polymers are thus cross-linked with diamines, diols, or disulfides. Alternatively, activated dicarboxylic acids are used to cross-link amino- or hydroxyl- or thiol-containing polymers.

In combination with any of the above or below embodiments, the degree of cross-linking is preferably 5% to 30%, more preferably 7% to 20%, and most preferably 10% to 15%.

Any solvent may be used for the synthesis, which does either not react or only slowly reacts with the cross-linker and the cross-linkable polymer under the conditions of preparation, and which dissolves said reactants preferably to at least 1% (w/v) solution. Slowly in this context means that at the selected temperature no visible gelling occurs before at least 30 minutes, using only the polymer cross-linker solution as demonstrated with Comparative Example 1.

In combination with any of the above or below outlined embodiments, the amount of cross-linked polymer immobilized inside the pores of the support material is preferably at least 1% w/w (weight of polymer and cross-linker/weight of the dried composite material), more preferably between 5% and 10% w/w, and is preferably less than 25% w/w.

The range of temperature for the synthesis process is preferably between 20° C. and 180° C., more preferably between 40° C. and 100° C., and most preferably between 50° C. and 70° C.

The related reaction time is preferably between 1 hour and 100 hours, more preferably between 8 hours and 60 hours and most preferred between 18 hours and 48 hours.

Abbreviations and Definitions

Partial volumes (µl), necessary in order to obtain the porosity data of an adsorbent, measured with a packed chromatographic column by injecting molecular standards of defined hydrodynamic radii $R_h$. The volumes have been determined by multiplying the signal time with the flow rate.

$V_e$

The net elution volume $V_e$ is obtained when the extra column volume of the chromatographic system has been subtracted from the gross elution volume. $V_e$ is identical to the total void volume of a column $V_o$. $V_{en}$ is the elution volume of an individual standard n.

$V_o$

The total void volume of a column is the sum of the pore volume $V_p$ and the interstitial volume $V_i$.

$V_i$

The interstitial volume $V_i$ is the volume between the particles.

$V_p$

Figure 3:
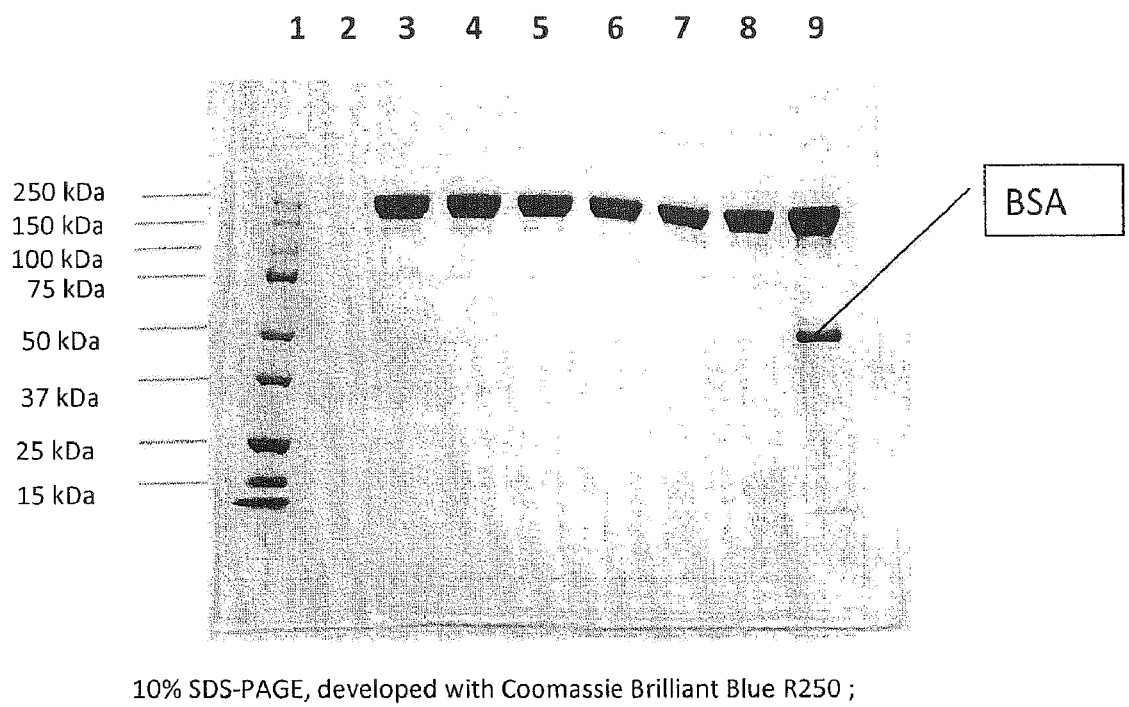

The pore volume $V_p$ of the adsorbent is comprising the total porous space.

hIgG polyclonal human immunoglobulin G
S-layer proteins, piece of cell surfaces
Materials
Cell Culture Supernatants (CCS)
CHO-K1, Invivo, Berlin, batch RP SZ 292/01
Mock Media of the Cell Line CHO-K1
Conductivity: 15 mS/cm, pH 7.0
HCP content 120 µg/ml, DNA content 1000 ng/ml.
Used for the depletion experiments of Tables 1.1 and 1.2
CCS BHK-21, Invivo, Berlin, batch RP SZ 352/01 Mock Media of the Cell Line BHK-21 contains 5% of BSA used for the Bovine Serum Albumine (BSA) depletion as shown in FIG. 3.

Feed

The particular CCS was spiked with 2 mg/ml of hIgG from human blood plasma (Octagam, 10% solution, Octapharma, Vienna).

Octagam contained 2.5%-3.5% of aggregates according to analysis by SEC.

Support Material

Silica Gel Davisil LC 250 (W. R. Grace), average nominal pore size 250 Å, particle size 40-63 µm (lot: 1000241810).

Eurosil Bioselect 300-5, 5 µm, 300 Å, Knauer Wissenschaftliche Geräte, Berlin, Germany.

Polymers

Poly(vinylformamid-co-polyvinylamin) solution in water, Lupamin 45-70 (BASF) supplier: BTC Europe, Monheim, Germany, partially hydrolysed for the embodiment of Example 1 by heating 1000 g of Lupamin 45-70 with 260 g of sodium hydroxide (10% w/v) at 80° C. over five hours. Finally the pH was adjusted to 9.5 with 170 g of a 10% hydrochloric acid. For Example 1a the untreated Lupamin 45-70 solution was used without sodium hydroxide hydrolysis and hydrochloric acid pH adjustment.

Cross-Linker

Hexanediol diglycidylether, Ipox RD 18, ipox chemicals, Laupheim (Germany)—lot: 16092)

Methods and Measurements

Size Exclusion Chromatography (SEC)

The concentration of hIgG in the feed and the recovery rate of hIgG in the purified solution have been determined with SEC under the following conditions:

Column: Tosoh TSK G3000 SWXL 7.8*300 mm (particle size 5 μm)

Mobile Phase: 10 mM sodium phosphate buffer, pH7.2+ 150 mM NaCl

Injection volume: 100 μL-sample diluted with the mobile phase.

Flowrate: 1 mL/min.

Detector: DAD 280 nm, hIgG solution (Octapharma) used as external standard.

Temperature: 20° C.+/−1° C.

Dry Mass Determination.

The composite is washed five times with each five bed volumes of water, then five times with each five bed volumes methanol. The dry mass of the support materials and of the composites was determined after drying a sample of 0.5 g under reduced pressure (0.1 mbar) at 80° C. for 12 hours, and then 2-3 times for 2 hours, until the weight was constant.

Pore Size Distribution and Pore Volume Fractions of the Various Composite Adsorbents The accessible pore volume fractions, which are correlated to the pore diameters and the exclusion limits for polymer molecules with various hydrodynamic radius have been determined using inverse Size Exclusion Chromatography (iSEC). For this purpose, the composite material was packed into a 1 ml (50×5 mm) chromatographic column, equilibrated with 20 mM aqueous ammonium acetate buffer, pH 6, and calibrated by applying two low molecular weight standards, and a selection of six commercial pullulane polymer standards of known defined average molecular weights $M_w$ (PPS, Mainz Germany, for details see Fig. Embodiments 1.1-1.4).

The $M_w$ determination of the pullulane standards was achieved at PSS by SEC with water, sodium azide 0.005% as mobile phase at a flow rate of 1 ml/min at 30° C. Three analytical columns, each 8×300 mm (PSS SUPREMA 10 μm 100 Å/3000 Å/3000 Å), have been used in in-line combination with an 8×50 mm pre-column (PSS SUPREMA 10 μm). Sample concentration was 1 g/l, injected volume 20 μl in each run. Detection was achieved with a refractive index (RI) monitor (Agilent RID), connected to a PSS WinGPC Data Acquisition system.

The pore volume fraction $K_{av}$, accessible for the particular standards in a particular composite material, was obtained by evaluation of the net elution volume $V_{en}$ (μl).

Accordingly, $K_{av}$ describes the fraction of the overall pore volume, a particular standard with given hydrodynamic radius $R_h$ can access. Methanol is used for the determination of the total liquid volume $V_t = V_e = V_0$ representing a $K_{av}$ value of 1. The pullulane standard of 210,000 Da is used to determine the interstitial volume $V_i$, between the packed composite particles, representing the liquid volume outside the particles, as it is already excluded from the pores (see also FIG. 1), thus representing a $K_{av}$ of 0 (0% of the pore volume). The difference between $V_o$ and $V_i$ is the pore volume $V_p$.

| iSEC Standards | $R_{hi}$ (nm) |
|---|---|
| Methanol | |
| Ethylene glycol | |
| Pullulan 6.2 kD | 2.13 |
| Pullulan 10 kD | 2.70 |
| Pullulan 21.7 kD | 3.98 |
| Pullulan 48.8 kD | 5.96 |
| Pullulan 113 kD | 9.07 |
| Pullulan 210 kD | 12.370 |

The partial pore volumes are defined as the respective volume fractions in the composite adsorbent, which can be accessed by not retained pullulane polymer standards, as well as by not retained smaller molecules. Not retained means, that in order to determine only the pore volume fractions, no interaction or binding of the respective standard occurs on the surface of a stationary phase. For the support material and the composites of the present invention this is the case for alcohols and hydrophilic carbohydrates, preferably pullulanes, exhibiting known hydrodynamic radii ($R_h$) in aqueous solvent systems.

The $R_h$ values of the pullulanes have been calculated from the molecular weight $M_w$ according to the empiric equation $R_h = 0.027 \, Mw^{0.5}$ (I. Tatarova et al., J. Chromatogr. A 1193 (2008), p. 130).

The $R_h$ value of IgG was taken from the literature (K. Ahrer et al., J. Chromatogr. A 1009 (2003), p. 95, Fig. 4).

The Distribution of Isoelectric Points. pI Values of the Host Cell Proteins in CCS CHO K1

Determined by Isoelectric Focusing (IEF) (for details see FIG. 2), calibrated with the standard proteins of known pI, as shown in the list (Example 4).

DNA Determination

The DNA quantification has been accomplished utilizing the Quant-iT PicoGreen dsDNA Reagent Kit, Life Technologies, Darmstadt (Germany), after DNA extraction with the DNA Extraction Kit, Cygnus Technologies, Southport (USA).

Host Cell Protein (HCP) Determination

The HCP quantification has been carried out with the Cygnus HCP ELISA Kit, CHO Host Cell Proteins 3rd Generation (F550), from Cygnus Technologies, Southport (USA).

EXAMPLES

Example 1

Preparation of Composite Adsorbent Batch 07 (Table 1)

704 μl (658 mg) of hexane diol diclycidylether (Mw 230.2, d=1.07 g/ml) cross-linker were dissolved in 42 ml water. This cross-linker solution was added to 15 ml of an aqueous solution of poly(vinylformamid-co-polyvinylamin) (Lupamin 45-70, partially hydrolysed, see materials). After mixing, the pH of 11 was adjusted with 3 ml of 0.5 M NaOH.

10 g of Silica Gel Davisil LC 250, 40-63 μm (W. R. Grace), dry powder, were sedimented into a flat bottom stainless steel dish with 8 cm diameter. The bed height was 8 mm. 39.5 g of the polymer-cross-linker solution were added and equally distributed over the silica, whereas the solution was rapidly soaked in the pores. The resultant paste was shaken for 1 min. on a gyratory shaker at 600 rpm, in order to obtain a homogeneous mass with smooth surface, covered by a liquid film of 1-3 mm. After closing the dish with a stainless steel lid, the paste was heated without further mixing or moving for 48 hours in a drying oven at 60° C. yielding 49.6 g of moist composite.

Subsequently, 41.3 g of this still wet paste were washed on a frit with five times 25 ml of water. Then the composite cake was suspended in 31.6 ml of 10% sulphuric acid and treated under smooth shaking over two hours at ambient temperature, in order to hydrolyse unreacted epoxy groups. Finally the product was washed on a frit with once more five times 25 ml of water and then stored in 20% ethanol/water.

Any other batches of Table 1 have been prepared this way, only varying the amount (volume) of cross-linking agent according to the targeted degree of cross-linking.

Reference Example 1

(Preparation of a Cross-Linked Polyvinylamine Gel)

In order to check the reaction without support material, 3 ml of the polymer-cross-linking agent solution of Example 1 was heated for 24 hours at 50° C. After six hours the gelation was visible. After 24 hours one piece of a transparent solid elastic gel was obtained.

Example 1a

Preparation of a Composite Adsorbent Using a Small Particle Support Material.

1 ml (935 mg) of hexane diol diclycidylether (Mw 230.2, d=1.07 g/ml) cross-linker were shaken with 59 ml water, forming a homogeneous emulsion. This cross-linker solution was added to 21 ml of an aqueous solution of poly(vinylformamid-co-polyvinylamin) (Lupamin 45-70, raw and untreated).

After mixing, a pH of 10 was adjusted with 0.5 M NaOH.

25 g of Silica Eurosil Bioselect 300-5, 5 µm, dry powder, were sedimented into a flat bottom stainless steel dish with 12 cm diameter. The bed height was about 15 mm. 46 g of the polymer-cross-linker solution were added and equally distributed over the silica, whereas the solution was soaked in the pores, forming a viscous, mucous mass. After adding of a 1.5 ml portion of the polymer-cross-linker solution and finally of 4 ml diluted polymer (1 ml of poly(vinylformamide-co-polyvinylamine) diluted with 3 ml of water) the suspension became smooth and homogeneous. The resultant paste was covered by a liquid film of about 1 mm height.

After closing the dish with a stainless steel lid, the batch was heated without further mixing or moving for 21 hours in a drying oven at 65° C. yielding 72 g of moist composite.

Subsequently, this paste was diluted with distilled water to a volume of 150 ml, and the resultant suspension was pumped into a 250×20 mm HPLC column, using a preparative HPLC pump. The packed composite bed was then washed with 250 ml of water. In order to hydrolyse unreacted epoxy groups, 100 ml of 2 n hydrochloric acid were pumped into the column and left there over two hours at ambient temperature. As the back pressure increased during this step and the subsequent rinsing with water, the packed composite was finally washed with 300 ml of ethanol, whereas the pressure dropped to 5 bars at a flow rate of 10 ml/min. The product was removed from the column and dried at ambient temperature. The nitrogen content was determined to 1.18%, and the carbon content to 2.99%.

Reference/Comparative Example 2

Preparation of the Composite Material Batch 19 Following WO 2013/037994 (Prior Art)

The pores of 10 g of Silica Gel Davisil LC 250, 40-63 µm have been completely soaked with the poly(vinylformamid-co-polyvinylamin) of Example 1. This intermediate product of step 1 was dried at 50° C., until the weight was constant. Afterwards this dried sorbent was suspended in isopropanol containing ethylene glycol diclycidylether (121 mg in 30 ml isopropanol) and agitated at 55° C. for 5 hours.

Afterwards this product of step 2 was filtered, washed with isopropanol, 0.5 M trifluoro acetic acid, water and methanol.

As shown in Figure Embodiments 1.3 and 1.4, the pore volume and the pore size distribution is different from the properties obtained with the composite material batch 07. For details see Table 2.

TABLE 2

Pore volume distribution according to FIG. Embodiments 1.2 and 1.4 determined with Pullulane standards; Support material Davisil LC 250 and composites materials batch 07 and batch 19

| Pullulane Mw range (kDa) Davisil LC 250 | $R_h$ range (nm) | % of pore volume | Pullulane Mw range (kDa) batch 07 | $R_h$ range (nm) | % of pore volume | Pullulane Mw range (kDa) batch 19 | $R_h$ range (nm) | % of pore volume |
|---|---|---|---|---|---|---|---|---|
| <6.2 | 0.17-2.13 | 29% | <6.2 | 0.17-2.13 | 52% | <6.2 | 0.17-2.13 | 79% |
| 6.2-10.0 | 2.13-2.70 | 11% | 6.2-10.0 | 2.13-2.70 | 22% | 6.2-10.0 | 2.13-2.70 | 15% |
| 10.0-21.7 | 2.70-3.98 | 24% | 10.0-21.7 | 2.70-3.98 | 22% | 10.0-21.7 | 2.70-3.98 | 4% |
| 21.7-48.8 | 3.98-5.96 | 24% | 21.7-48.8 | 3.98-5.96 | 3% | 21.7-48.8 | 3.98-5.96 | 1% |
| 48.8-113 | 5.96-9.07 | 12% | 48.8-113 | 5.96-9.07 | 1% | 48.8-113 | 5.96-9.07 | <1% |

The volume fraction between $R_h$=2 nm and $R_h$=4 nm is important as a capture space for proteins below 100,000 Da molecular weight. It is therefore advantageous to generate as much volume as possible in this range, in order to provide a high binding capacity for host cell proteins. Batch 07 exhibits about 44% of the total volume within said range, whereas the product of a two-step synthesis batch 19 exhibits only a pore volume fraction of about 19%. In addition, there is only a pore volume fraction of 4% with batch 19 in the $R_a$ range between 2.7 nm and 4 nm.

Basically, the data of batches 07 and 19 show that a different pore size distribution and thus a different morphology of the resulting composites is created by the different way of synthesis.

Example 2

Analysis of the separation capability of the composite materials listed in Table 1.1, prepared according to Example 1 and of the comparative commercial materials listed in Table 1.2.

In order to measure the separation capability of the composite material, the degree of depletion (separation) of impurities or undesired compounds from the target substance is determined. For this purpose the concentration of individual components or of substance classes in the feed is determined using selective assays. After the separation step this concentration measurement is repeated with the purified fraction. Thus, it is possible to calculate both purity and recovery from these concentrations and the related volumes.

Cygnus CHO HCP $3^{rd}$ Generation Elisa assay was used to determine the efficiency of purification, by comparing the raw feed solution to the depleted supernatant fraction, after specified contact time with the new composite material, with respect to the host cell protein (HCP) removal.

Quant-iT PicoGreen dsDNA Reagent Kit was applied to determine dsDNA. The hIgG recovery rate was determined by quantitative SEC.

General Depletion Procedure

The feed was an untreated and undiluted Cell Culture Supernatant CHO-K1, spiked with 2 mg/ml hIgG (polyclonal antibody Octagam, for details see Materials). 400 mg of the moist, equilibrated adsorbent were incubated with 2 ml of the feed using a Falcon tube or a centrifugation tube. After 5 min of gentle shaking the supernatant was separated by centrifugation for subsequent analysis.

The recovery of hIgG was determined by quantitative SEC (for equipment see under Methods and Measurements). The main peak (97-98%) in the chromatogram relates to the monomer and an earlier eluting peak (2-3%) to the immunoglobulin aggregates, which already were present in the original hIgG (Octagam) preparation. Calibration and recovery determination refer to the main peak.

As the adsorbent was in a wet state before contacting with the feed, the related void volume is increasing the total liquid volume. Thus the substance concentrations will decrease. The void volume is typically 70% to 90% of the resin weight. Accordingly were the final substance concentrations corrected by the respective dilution factor after the depletion step.

During this purification procedure the amount of aggregates were found constant. In contrast, there is often aggregate formation observed using the prior art adsorbents and separation protocols.

Macromolecular DNA is much larger than hIgG and is thus generally excluded from the composite pore system. Also hIgG is excluded as it is shown in Example 3.

Results

The results for composite adsorbents obtained after pore filling of the support material Silica Gel Davisil LC 250 40-63μ with hydrolysed poly(vinylformamid-co-polyvinylamin) Lupamin 45-70 (BASF) and various amounts of the cross-linking agent hexanediol diglycidyl ether are shown in Table 1.

The volume of cross-linker added was varied to obtain the indicated degrees of cross-linking. The volume of 704 μl used to prepare composite batch 07 is representing a 10% cross-linking degree. All other conditions were as in Example 1.

The ratio of feed volume and adsorbent mass was 5:1 (2 ml feed: 0.4 g adsorbent).

All adsorbents were equilibrated with 50 mM ammonium acetate buffer, pH 6, prior to contacting with the feed.

TABLE 1.1

Impurity depletion as a function of cross-linking

| Batch No. according to Example 1 | Amount of Cross-linking agent | HCP depletion (%) | DNA depletion (%) | Recovery hIgG (%) SEC |
|---|---|---|---|---|
| 06 | 5% | 99.8 | 92.2 | 83 |
| 09 | 7.5% | 91.5 | 92.1 | 80 |
| 07 | 10% | 98.7 | 92.7 | 95 |
| 15 | 10% | 98.1 | 94.5 | 91 |
| 08 | 15% | 95.0 | 95.0 | 96 |
| 10 | 15% | 90.8 | 94.3 | 89 |
| 11 | 20% | 94.2 | 98.7 | 90 |

DNA analysis was carried out with Quant-iT PicoGreen assay after DNA extraction (see methods).

HCP analysis was carried out with Cygnus HCP ELISA, CHO $3^{rd}$ Generation (F 550), see methods Comparative Example 3

Analysis of the Separation Capability of Commercially Available Amino-Containing Adsorbents The same depletion procedure as described in Example 2 was used to measure the separation capability of commercially available amino-containing adsorbents, exhibiting positively charged groups under the specified test conditions.

Table 1.2 shows the results for the commercially available amino-containing anion exchange adsorbents Toyopearl AF Amino 650 M, Tosoh Bioscience, Griesheim (Germany); Toyopearl DEAE 650 M, Tosoh; and Q Sepharose FF, GE Healthcare, Little Chalfont (UK).

The ratio of feed volume and adsorbent mass was 5:1 (2 ml feed: 0.4 g adsorbent). All adsorbents were equilibrated with 50 mM ammonium acetate buffer, pH 6.5, prior to contacting with the feed.

TABLE 1.2

Depletion of impurities from feed with commercially available amino-containing adsorbents

| Comparative Examples | Support material | HCP depletion (%) | DNA depletion (%) |
|---|---|---|---|
| Toyopearl AF Amino 650 M | Toyopearl HW 65 | 47.9 | 92.0 |
| Toyopearl DEAE 650 M | Toyopearl HW 65 | 53.4 | 93.4 |
| Q Sepharose FF | Sepharose | 81.8 | 95.6 |

DNA analysis was carried out with Quant-iT PicoGreen assay after DNA extraction (see methods). HCP analysis was carried out with Cygnus HCP ELISA, CHO $3^{rd}$ Generation (F 550), see methods.

Results

As can be seen from Table 1.1, a hIgG recovery between 80% and 96% was achieved, together with the capability of the composite adsorbents of the present invention to simultaneously deplete HCPs and DNA to high extent (more than 92%).

It has been shown by inverse size exclusion chromatography (iSEC) that pullulane polymer standards with a hydrodynamic radius $R_h>4$ nm were excluded to >90% from the pores of the composite materials (see Fig. Embodiment 1.2). IgGs feature a $R_h$ of 4.5-5 nm and are thus also excluded from these pores (for details see Example 3).

In addition, it has been shown that the dynamic binding capacity of DNA (sodium salt from calf thymus, Type 1, fibers, Sigma) is approximately 1.2 mg/ml of composite. DNA portions subsequently injected are eluted in the interstitial volume $V_i$ (volume between the packed particles) of about 0.5 ml from a 1 ml column, whereas smaller polymer standards and methanol have still access to the internal pore volume. This shows that macromolecular DNA is only bound to the external surface of the composite adsorbent. Macromolecular DNA is much larger than hIgG and is thus generally excluded from the composite pore system. Also hIgG is excluded as it is shown in Example 3.

Example 3

Determination of the Binding Capacity for hIgG

The purpose of this experiment was to show that hIgG is excluded from the adsorbent pores, while only a very small amount is bound to the exterior of the adsorbent.

About 1 ml of the adsorbent batch 07 (Example 1 and Table 1.1) was packed into a 1 ml column (50×5 mm) and equilibrated with 20 mM ammonium acetate buffer, pH 6.

The hIgG test solution (c=2 mg/ml) was prepared from the 10% Octagam stock solution by dilution with 50 mM ammonium acetate buffer, pH 6.5 (buffer A).

The flow rate during the loading step was 0.2 ml/min and 1 mL/min during the wash.

Optical density in the eluate was monitored at 280 nm.

The gross elution volume consists of the two contributions intra column volume, i.e., liquid volume of the packed column $V_t=V_e$ plus extra column volume of the chromatographic system.

The total liquid volume $V_t$ of the packed column was determined as 972 µl, by running a sample of methanol, the interstitial volume $V_i$ was determined with Pullulan 48.800 Da. as 523 µl. The pore volume of the adsorbent $V_p$ is the difference, hence 449 µl.

The elution of the hIgG signal began at a volume of 630 µl (FIG. 4.1). From this gross elution volume, 44 µl were subtracted, representing the extra column volume of the chromatographic system. Accordingly the net retention volume for hIgG was 586 µl. This volume is significantly smaller than the column liquid volume $V_t$ of 972 µl indicating that the hIgG has no access into the pore system.

At the moment of the breakthrough the interstitial volume $V_i$ of 523 µl was filled with unbound hIgG. Accordingly the quantity of hIgG, which initially had been contained in the difference volume of 586 µl–523 µl=63 µl, has been bound to the composite batch 07 at the moment of breakthrough. Thus 126 µg were bound to 1 ml of composite. This small adsorbed quantity is probably related to antibodies with a pI<6, binding to the low area outer surface of the particles under condition of the actual salt concentration.

Additional Substance Injections after Saturating the Composite with hIgG.

After saturating this column, packed with the composite batch 07, with hIgG, five equal 50 µg injections of the hIgG solution have been made under the same buffer conditions, but with a flow rate of 1 ml/min (FIG. 4.2).

All chromatograms were identical. The breakthrough occurred already after 0.45 min, the peak maximum was reached at 0.572 min or 572 µl. Subtracting the extra column volume of 44 µl, a volume of 528 µl was obtained, well matching the interstitial void volume $V_i$ in the column.

This is proof for hIgG not additionally binding to the composite, once saturated with hIgG and for hIgG exclusion from the pore system.

Accordingly the small amount of adsorbed hIgG was bound only to the outer surface of the particles, while the major portion of hIgG with a hydrodynamic radius $R_h$ between 4.5 and 5.5 nm remains unbound and is, moreover, unable to enter the pores of the composite, which are sized below an $R_h$ of 4 nm (Embodiments of FIG. 1).

From FIG. 1 it can be concluded that molecules with an $R_a$ larger than 4 nm are generally excluded from at least 90% of the pores of the composite.

Example 4

Characterization of CCS CHO-K1 by Isoelectric Focusing and Depletion of Basic (Positively Charged) Host Cell Proteins.

Isoelectric Focusing (IEF) was used in order to determine the charge heterogeneity of the proteins in CCS as well as to demonstrate the presence of basic proteins above pI 7.5 therein.

Figure 2:
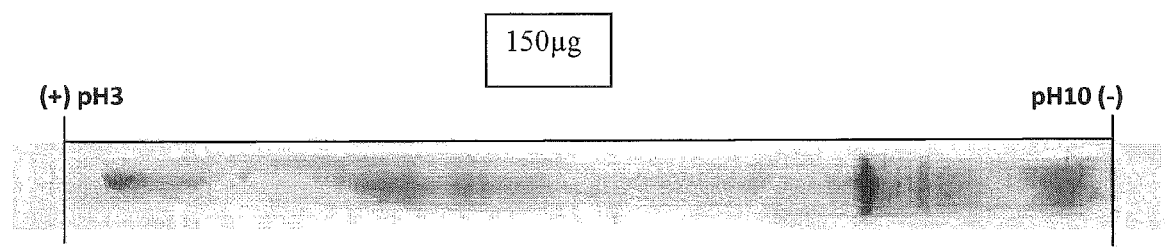
Figure 2:
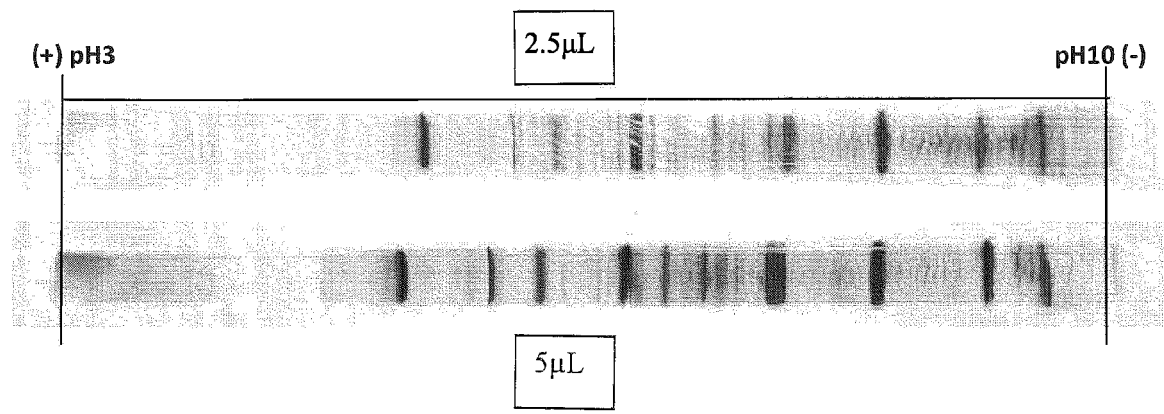

The pH range of the IEF strips was calibrated utilizing a commercial kit containing proteins with known isoelectric points. The stained gel of the mock CCS, which was investigated under the same conditions, shows a broad distribution of bands between pI 3 and pI 10 and a fraction of proteins with high pI above 8. Accordingly a significant amount of the host cell proteins (HCP) in the CCS is basic (FIG. 2).

According to quantitative HCP ELISA hIgG purified from hIgG supplemented CCS showed a HCP depletion of, e.g., 98.7% (Table 1.1, batch 07), demonstrating that the major portion of the basic host cell proteins present in crude CCS, were thus removed. The individual IEF runs were calibrated using nine protein standards of known pI (Biorad), as listed below.

Constituent Proteins of the IEF Standard Used for the Calibration of pI Values:

| Proteins | PI | Mw (Da) |
|---|---|---|
| Phycocyanin (3 bands) | 4.45 | 232 000 |
|  | 4.65 |  |
|  | 4.75 |  |
| B-Lactoglobulin B | 5.10 | 18 400 |
| Bovine carbonic anhydrase | 6.00 | 31 000 |
| Human carbonic anhydrase | 6.50 | 28 000 |
| Equine myoglobin (2 bands) | 6.80 | 17 500 |
|  | 7.00 |  |
| Human hemoglobin A | 7.10 | 64 500 |
| Human hemoglobin C | 7.50 | 64 500 |
| Lentil lectin (3 bands) | 7.80 | 49 000 |
|  | 8.00 |  |
|  | 8.20 |  |
| Cytochrome c | 9.60 | 12 200 |

Conditions for the isoelectric focusing (IEF) K1 (GEL: 4-15% Mini-PROTEAN® TGX™ Gel (Biorad), 7 cm IPG/prep well, 250 µL, Strips: 7 cm IPG strip pH3 to pH10 linear gradient, Staining method: Coomassie Brilliant Blue R-250) of the CCS CHO shows a broad distribution of bands between pI 4 and pI 10 (see FIG. 2) and a basic fraction of proteins above pI 7.5.

Conclusion:

Unexpectedly, the amino groups containing composite does not only bind anionic species (pI 2-6), but also cationic (pI 8-11) and neutral compounds, most importantly from the group of HCPs. These results are obtained with the immobilized polyvinylamine positively charged, as it generally is, when using 50 mM ammonium acetate buffer, pH<7.5, for the composite equilibration. If equilibrated at pH 6.5 with 50 mM ammonium acetate buffer the composite removed up to 99.8% of the HCP in CCS CHO K1 (Table 1.1, batch 06). Therefore, it was surprisingly found, that the depletion of HCPs and other impurities appears vastly independent of their isoelectric point.

In comparison with the conventional strong anion exchanger Q Sepharose, which removed only 81.8% of the HCP, under the same conditions (see Table 1.2), the poly(vinylamine)-containing silica adsorbent material of the present invention depleted up to 99.8% of the total HCP inventory in the presence of 2 mg/ml of polyclonal hIgG, the latter recovered to up to 96%.

Example 5 and Explanation of FIG. 3

Depletion of bovine serum albumin (BSA) from the cell culture supernatant CCS BHK-21 (see materials), after treatment according to Example 2 with the two composite batches 07 and 08 at two pH conditions, and with or without salt.

FIG. 3 shows that with a feed (lane 9) composed of CCS Invivo BHK-21 containing about 50 mg/ml of BSA as a nutrient and spiked with hIgG (2 mg/mL), BSA is depleted down to the detection level in one batch step (lanes 3-8). The depletion was carried out according to Example 2 with the composites batch 07 and 08 of Table 1.1 in six independent experiments.

Beyond the usual equilibration with 50 mM ammonium acetate at pH 6.5 (lanes 5 and 8), 50 mM ammonium acetate pH 6.5 with 150 mM of NaCl was used for the equilibration of the composite (lanes 4 and 7). In addition, both composites have been equilibrated with 50 mM ammonium acetate at pH 7.4, 150 mM NaCl (lanes 3 and 6).

Thus it was demonstrated that the quantitative removal of BSA works also in the presence of salt and at a higher pH.

Purified samples applied to the particular lane 3-8 of the SDS PAGE, feed on lane 9

1, marker proteins (Bio Rad, Precision Plus Protein)
2, blank
3, Purification with batch 08 (composite equilibrated with 50 mM aqueous ammonium acetate pH 7.4, 150 mM sodium chloride)
4, Purification with batch 08 (composite equilibrated with 50 mM aqueous ammonium acetate pH 6.5, 150 mM sodium chloride)
5, Purification with batch 08 (composite equilibrated with 50 mM aqueous ammonium acetate pH 6.5, without salt)
6, Purification with batch 07 (composite equilibrated with 50 mM aqueous ammonium acetate pH 7.4, 150 mM sodium chloride)
7, Purification with batch 07 (composite equilibrated with 50 mM aqueous ammonium acetate pH 6.5, 150 mM sodium chloride)
8, Purification with batch 07 (composite equilibrated with 50 mM aqueous ammonium acetate pH 6.5, without salt)
9, Feed CCS Invivo BHK-21 (batch RP_SZ_352/01)+ hIgG 2 mg/mL contains 5% (w/v) Bovine Serum Albumine (BSA)

Fig. Embodiment 1.1

Composite Adsorbent batch 07. Plot of the net elution volume $V_e$ (μl) of methanol, ethylene glycol, and six pullulane standards with known different hydrodynamic radii ($R_{hi}$), versus $R_{hi}$.

The pore volume $V_p$ of the adsorbents and the interstitial volume $V_i$ between the particles are determined by iSEC (diagram $V_e$), using a packed column of a 1 ml (50×5 mm) nominal resin volume. In the column, packed with the support material Davisil LC 250 and the various composite materials, total liquid volumes $V_t = V_e$ ($V_e$ is the net elution volume determined, when the extra column volume has been subtracted) between 965 μl and 998 μl have been measured, completely accessible for the smallest standard methanol. Interstitial volumes $V_i$ between the particles have been determined between 450 μl and 530 μl. The deviations in the particular volume fractions are due to small differences in the amount of packed material as well as in the packing density of the individual column. Standards with $R_h > 9$ nm are not able to access the pores of the silica Davisil LC 250 and are eluting within the same volume after migrating solely after passing the interstitial volume $V_i$ of 449 μl. E.g. the total pore volume $V_p$ of e.g. Davisil LC 250 silica in the column of Fig. Embodiment 1.1 is the difference of 998 μl−449 μl=549 μl. The calibrated pullulane standards are penetrating a volume fraction according to their particular hydrodynamic radius $R_h$. The volume ratios of the various composites are measured in the same way.

Fig. Embodiment 1.2

Composite Adsorbent batch 07. Plot of the distribution coefficient ($K_{av}$ value, i.e., pore volume distribution fraction, see methods; $K_{av}$ is equivalent to the fraction of pore volume available for an individual substance) versus the hydrodynamic radius $R_{hi}$ of the same test substances as in Fig. Embodiment 1.1.

The distribution coefficient $K_{av}$ is defined as the pore volume fraction $V_{en}$ available for the particular molecular standard n above a certain pore diameter, i.e., $K_{av} = V_{en} - V_i / V_e - V_i$. The upper iSEC curve (Silica 250) shows the pore size distribution of the support material Davisil LC 250, with an exclusion limit at $R_h = 9$ nm and an accessible pore volume fraction $K_{av}$ of 0.36 (36% of the total pore volume is given between 4 nm and 9 nm hydrodynamic radius of the polymer standard) at a $R_h$ of 4 nm. That means that 36% of the pore volume is accessible for a molecule with a $R_h$ of 4 nm.

The three lower curves show the porosity of the embodiment batch 07 (Table 1.1) obtained with repetitive runs. After the immobilization of the polymer only<5% ($K_{av} = 0.05$) of the pores exhibit a value of 4 nm or greater.

This is the physical proof for filled/full or occupied pores under the conditions of use, with respect to the accessibility for a molecule of particular diameter:

Whereas in the starting material Davisil LC 250 more than 36% of pores are found in the range between 4 and 9 nm, more than 30% of the corresponding pore volume is absent in the product batch 07 after immobilisation of the cross-linked polymer mesh. This is obviously due to the space occupation and partitioning of just this volume by the polymer network.

With other words: >30% of the pore volume of the Davisil LC 250 between 4 nm and 9 nm, which initially represented>36% of the total pore volume, has disappeared, because the pores of this size have been occupied by the polymeric mesh, exhibiting significantly smaller pores. All of the smaller support pores are containing the polymeric mesh, too. Accordingly the porosity of the composite is established by the internal pores of the polymeric mesh (like a small sponge) in its swollen state at a pH of 6. The low molecular weight standard methanol, however, enters the entire pore volume of the support material as well as the entire pore volume of the composite. Hence, the slope of the composite porosity curve is significantly steeper than the slope of the Davisil LC 250 curve.

Provided that only the walls of the Davisil LC 250 would have been coated, the $K_a$y curve of the composite would be anticipated parallel to the Davisil LC 250 curve, at least in the range between $R_h$ of 4 nm to 9 nm, because there would always a gap be left behind in the center of each pore.

The described steric exclusion effect is responsible for the purification capabilities of the polymeric mesh inside the composite, with respect to, e.g., antibodies left vastly unbound in the exterior volume of the packed or suspended new composite material, while lower molecular mass components, e.g., host cell proteins enter the pores of the immobilized polymer, where they may become captured.

It is crucial that about 40% of the composite pores are accessible for molecules with $R_h$ between 2 nm and 4 nm, comprising the hydrodynamic radii of most proteins below 100.000 molecular mass. Within this fraction of the pores most Host Cell Proteins are trapped, including the positively charged basic ones with a pI>7.0, although the polymer is positively charged, too (see Example 3 and FIG. 2), under the usual working conditions.

Fig. Embodiment 1.3

Composite Adsorbents batch 19, comparative example, and Composite Adsorbent batch 07, example of the present invention. Plot of the net elution volume $V_e$ (µl) of methanol, ethylene glycol, and six pullulane standards with known different hydrodynamic radii ($R_{hi}$), versus $R_{hi}$.

Fig. Embodiment 1.4

Composite Adsorbents batch 19, comparative example, and Composite Adsorbent batch 07, example of the present invention. Plot of the distribution coefficient ($K_{av}$ value, i.e., pore volume distribution fraction, see methods; $K_{av}$ is equivalent to the fraction of pore volume available for an individual substance) versus the hydrodynamic radius $R_{hi}$ of the same test substances as in Fig. Embodiment 1.1.

In contrast to composite material batch 07, the batch 19, synthesized in two steps inclusive preliminary drying after the first step, shows a very different porosity in the nanometer range. Only 4% of the pore volume are available between a hydrodynamic radius of 2.7 nm and 4 nm, whereas batch 07 offers a volume fraction of 22% in the same range. For details see Table 2.

FIG. 2

Isoelectric focusing (IEF) of a concentrated solution of cell culture supernatant (CCS) from CHO K1 cell line according to Example 4, typical for visualization of the pI spectrum of the host cell proteins (HCP) in this kind of sample. A significant number of neutral and basic host cell proteins, focusing closely together in the pI range between 7 and 10 are found.

Isoelectric Focusing (IEF) was used in order to determine the charge heterogeneity of the proteins in CCS as well as to demonstrate the presence of basic proteins above pI 7.5 therein.

The pH range of the IEF strips was calibrated utilizing a commercial kit containing proteins with known isoelectric points. The stained gel of the mock CCS, which was investigated under the same conditions, shows a broad distribution of bands between pI 3 and pI 10 and a fraction of proteins with high pI above 8. Accordingly a significant amount of the host cell proteins (HCP) in the CCS is basic.

FIG. 3

Depletion of bovine serum albumin (BSA) from the cell culture supernatant CCS BHK-21, after treatment according to Example 5 with the two composite batches 07 and 09 at two pH conditions, and with or without salt.

FIG. 4

Exclusion of hIgG from the adsorbent pores according to Example 3, while only a minor portion is bound to the exterior surface of the adsorbent.

Explanation to FIG. 4, See Also Example 3

The purpose of this experiment was to show that hIgG is excluded from the adsorbent pores, while only a very small amount is bound to the exterior of the adsorbent.

Under the conditions of a dynamic capacity measurement, the moment of the breakthrough (FIG. 4.1) the interstitial column volume $V_i$ of 523 µl was filled with unbound hIgG. Accordingly the quantity of hIgG, which initially had been contained in the difference between the elution volume and the void (586 µl–523 µl=63 µl) has been bound to the composite batch 07 at the moment of breakthrough. Thus 126 µg were bound to 1 ml of composite.

After saturating this column, packed with the composite batch 07, with 126 µg of hIgG, five equal 50 µg injections of the hIgG solution have been made under the same buffer conditions, but with a flow rate of 1 ml/min (FIG. 4.2).

All chromatograms were identical. The breakthrough occurred already after 0.45 min, the peak maximum was reached at 0.572 min or 572 µl. Subtracting the extra column volume of 44 µl, a volume of 528 µl was obtained, well matching the interstitial void volume $V_i$ in the column.

FIGS. 5 to 12 summarize the objects of the present invention, the general concept, the working principle, the batch depletion materials in one potential process, the batch results, the batch results in terms of recovery hIgG, the batch results in depletion of HCP and DNA, and the Summary.

In another aspect, the invention relates to the following items:

1. A method for recovering a target protein from a feedstock, said feedstock being in the form of a solution or suspension, and comprises at least one target protein and at least one impurity compound selected from host cell proteins (HCP), DNA, RNA or other nucleic acid, or a combination of two or more thereof, and optionally comprising albumins, endotoxins detergents and microorganisms, or fragments thereof, or a combination of two or more thereof, said method comprising the steps of:
   i) contacting said feedstock with a polymeric mesh comprising at least one amino polymer for a sufficient period of time, wherein at least one impurity compound is retained;
   ii) subsequently, separating the polymeric mesh from the purified feedstock containing at least one target protein;
   iii) optionally, isolating the target protein from the feedstock.
2. The method according to item 1, wherein the at least one impurity compound retained by the polymeric mesh comprising at least one amino polymer exhibits a hydrodynamic radius $R_{h1}$ that is lower than the hydrodynamic radius of the target protein remaining in the purified feedstock,
preferably wherein the at least one impurity compound retained by the polymeric mesh comprising at least one amino polymer exhibits a hydrodynamic radius $R_{h1}$ below 4 nm, and wherein the at least one target protein remaining in the purified feedstock exhibits a hydrodynamic radius $R_{h1}$ of 4 nm or greater than 4 nm.
3. The method of any one of the previous items, wherein the polymeric mesh comprising at least one amino polymer is equilibrated to a pH below 8 in advance to the contacting with the feedstock.
4. The method according to any of the previous items, wherein the target protein is an antibody.
5. The method according to any of the previous items, wherein compounds with a pI of 7 or above 7 are depleted by the polymeric mesh comprising at least one amino polymer, which has been equilibrated to a pH below 8, to at least 50% of their initial concentration.
6. The method according to item 5, wherein said impurity compounds are host cell proteins.
7. The method according to any of the previous items, wherein the host cell proteins are depleted from the feedstock to at least 90% of their initial concentration.
8. The method according to any of the previous items, wherein the feedstock is a fermentation broth suspension.
9. The method according to any of the previous items, wherein a one-step batch adsorption process is used within the procedures of i) and ii), characterized in that there is no convective transport applied.
10. The method according to any of the previous items, wherein the polymeric mesh is part of a composite material.
11. The method according to any of the previous items, wherein the amino polymer is either poly(vinylamine) or poly(vinylformamide-co-vinylamine), or a mixture thereof.
12. A process for the synthesis of a composite material, comprising the steps of:
i) filling at least the pore volume of a support material with a solution of at least one cross-linkable polymer or co-polymer and at least one cross-linking agent,
ii) and in situ immobilizing said cross-linkable polymer by cross-linking, wherein the support material is particulate, pellicular or monolithic.
13. The process according to item 12, wherein the cross-linkable polymer is poly(vinylformamide-co-vinylamine) or poly(vinylamine), or a mixture thereof.
14. A composite material prepared according to item 12 or 13.

The invention claimed is:
1. A method for recovering a target protein from a feedstock, said feedstock comprising said target protein and at least one impurity compound selected from host cell proteins (HCP), DNA, RNA or other nucleic acid, or a combination of two or more thereof, the feedstock being in the form of a solution or suspension, and the target protein being characterized by a hydrodynamic radius $R_{h1}$ and the impurity compound being characterized by a hydrodynamic radius $R_{h2}$, wherein $R_{h1}>R_{h2}$, the method comprising the following steps (i) to (iv):
(i) providing a polymeric mesh comprising at least one crosslinked polymer containing positively charged amino groups, the polymeric mesh being characterized by a pore size exclusion limit $R_{hi}$ which can be set variably;
(ii) adapting the variable pore size exclusion limit $R_{hi}$ of the polymeric mesh to the hydrodynamic radii $R_{h1}$ and $R_{h2}$ such that $R_{h2}<R_{hi}$ and $R_{h1}>R_{hi}$;
(iii) contacting the polymeric mesh with the feedstock for a time sufficient to allow retaining the impurity compound in the polymeric mesh and excluding the target protein from the polymeric mesh;
(iv) separating the polymeric mesh containing the retained impurity compound from the feedstock containing the excluded target protein in order to obtain a purified feedstock.
2. A method for recovering a target protein from a feedstock, said feedstock comprising said target protein and at least one impurity compound selected from host cell proteins (HCP), DNA, RNA or other nucleic acid, or a combination of two or more thereof, the feedstock being in the form of a solution or suspension, and the target protein being characterized by a hydrodynamic radius $R_{h1}$ and the impurity compound being characterized by a hydrodynamic radius $R_{h2}$, wherein $R_{h1}>R_{h2}$, the method comprising the following steps (i) and (iii) to (iv):
(i) providing a polymeric mesh comprising at least one crosslinked polymer containing positively charged amino groups, the polymeric mesh being characterized by a pore size exclusion limit $R_{hi}$ such that $R_{h2}<R_{hi}$ and $R_{h1}>R_{hi}$;
(iii) contacting the polymeric mesh with the feedstock for a time sufficient to allow retaining the impurity compound in the polymeric mesh and excluding the target protein from the polymeric mesh;
(iv) separating the polymeric mesh containing the retained impurity compound from the feedstock containing the excluded target protein in order to obtain a purified feedstock.
3. The method of claim 1, wherein said step (i) or said step (ii) or said step (i) and said step (ii) further comprise(s) one or more of the following: varying a structure of the polymer, selecting a cross-linker used to generate the polymeric mesh, selecting a degree of cross-linkage of the polymeric mesh, and controlling a degree of swelling of the polymeric mesh by varying a solvent for preparation and use of the polymeric mesh, particularly varying a pH of the solvent and thus a degree of protonation of the polymeric mesh.
4. The method of claim 1, comprising: equilibrating the polymeric mesh obtained in said step (ii) prior to the contacting in said step (iii) to a pH below 8; or method of claim 2, comprising: equilibrating the polymeric mesh provided in said step (i) prior to the contacting in said step (iii) to a pH below 8.
5. The method of claim 4, said step (iii) comprising: depleting neutral or positively charged compounds with a pI (isoelectric point) of 7 or above 7 by the equilibrated polymeric mesh.
6. The method of claim 1, wherein the variable pore size exclusion limit $R_{hi}$ of the polymeric mesh provided in said step (i) or adapted in said step (ii) is set or adapted to a range of from 1 nm to 20 nm.
7. The method of claim 1, wherein the variable pore size exclusion limit $R_{hi}$ of the polymeric mesh provided in said step (i) or adapted in said step (ii) is set or adapted to a range of from 3 nm to 10 nm.

8. The method of claim 6, wherein the impurity compound to be retained in the polymeric mesh is selected from an impurity compound having a hydrodynamic radius $R_{h2}$ below 4 nm.

9. The method of claim 8, wherein said impurity compound is a host cell protein.

10. The method of claim 9, wherein the target protein is an antibody.

11. The method of claim 1, wherein the feedstock is a fermentation broth suspension.

12. The method of claim 1, wherein said steps (iii) and (iv) are performed as a one-step batch process without applying convective transport.

13. The method of claim 1, wherein the polymeric mesh is part of a composite material.

14. The method of claim 1, wherein said step (i) comprises: converting poly(vinylamine) or poly(vinylformamide-co-vinylamine), or a mixture thereof to said cross-linked polymer containing positively charged amino groups.

15. The method of claim 2, wherein the pore size exclusion limit $R_{hi}$ of the polymeric mesh provided in said step (i) is in a range of from 1 nm to 20 nm.

16. The method of claim 2, wherein the pore size exclusion limit $R_{hi}$ of the polymeric mesh provided in said step (i) is in a range of from 3 nm to 10 nm.

17. The method of claim 1, further comprising the following step (v):

(v) isolating the target protein from the purified feedstock.

18. The method of claim 1, wherein said feedstock further comprises albumins, endotoxins, detergents and microorganisms, or fragments thereof, or a combination of two or more thereof.

19. The method of claim 2, further comprising the following step (v):

(v) isolating the target protein from the purified feedstock.

20. The method of claim 2, wherein said feedstock further comprises albumins, endotoxins, detergents and microorganisms, or fragments thereof, or a combination of two or more thereof.

\* \* \* \* \*